United States Patent
Grimes et al.

(10) Patent No.: US 6,397,661 B1
(45) Date of Patent: Jun. 4, 2002

(54) REMOTE MAGNETO-ELASTIC ANALYTE, VISCOSITY AND TEMPERATURE SENSING APPARATUS AND ASSOCIATED METHODS OF SENSING

(75) Inventors: Craig A. Grimes; Plamen G. Stoyanov, both of Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/223,689

(22) Filed: Dec. 30, 1998

(51) Int. Cl.$^7$ .............................. G01N 9/10; G01N 11/16
(52) U.S. Cl. ..................... 73/24.06; 73/30.04; 73/30.05; 73/31.05; 73/32 A; 73/54.26; 73/61.79; 73/64.53; 324/207.13
(58) Field of Search ............................ 324/204, 207.13, 324/209, 235, 239, 633, 71.1; 73/54.01, 54.02, 54.41, 64.53, 865, 24.01, 31.05, 54.23–54.27, 54.38, 61.49, 52, 61.75, 61.79, 24.05, 24.06, 30.04, 30.02, 32 A

(56) References Cited

U.S. PATENT DOCUMENTS

| | | | |
|---|---|---|---|
| 4,041,769 A | * 8/1977 | November | ................... 73/32 A |
| 4,510,489 A | 4/1985 | Anderson, III et al. | ...... 340/572 |
| 4,660,025 A | 4/1987 | Humphrey | ................... 340/572 |
| 4,679,427 A | * 7/1987 | Kanda et al. | ................... 73/54 |
| 4,745,401 A | 5/1988 | Montean | ..................... 340/572 |
| 4,769,631 A | 9/1988 | Copeland | .................... 340/551 |
| 4,980,670 A | 12/1990 | Humphrey et al. | ......... 340/551 |
| 5,004,914 A | * 4/1991 | Vali et al. | ............... 250/227.27 |

OTHER PUBLICATIONS

Grate and Abraham, 3 *Sensors and Actuators B* pp. 85–111 (1991).
Zhou, et al., 35–36 *Sensors and Actuators B* pp. 176–182.
Nagasaki, et al., 29 *Macromolecules* pp. 5859–5863 (1996).
Grimes, et al., 33–5 *IEEE Transactions on Magnetics* (Sep./1997) pp. 3412–3414.
Stoyanov, et al., 34–4 *IEEE Transactions on Magnetics* pp. 1315–1317 (Jul. 1998).
Kikuchi, et al., 68–5 *Analytical Chemistry* pp. 823–828 (Mar./1996).
Sheppard, et al., 28 *Sensors and Actuators B* (1995) pp. 95–102.
Sheppard, et al., 10 *Sensors and Actuators B* (1993) pp. 73–77.
Gutiérrez, et al., 111 *Phys. Stat. Sol.* (a) (1989) pp. 279–283.
Barandiarán and Gutiérrez, 59 *Sensors and Actuators A* (1997) pp. 38–42.
Barandiarán, et al., 5 *Int. J. of Applied Electromagnetics in Materials* 75 (1994).

*Primary Examiner*—Hezron Williams
*Assistant Examiner*—Rose M. Miller
(74) *Attorney, Agent, or Firm*—Macheledt Bales LLP

(57) ABSTRACT

An analyte, viscosity, or temperature sensing apparatus for operative arrangement within a time-varying magnetic field, including a sensor with an outer surface that is chemically, frictionally, or thermally responsive and adhered to a base magnetostrictive element, and a receiver to measure a first and second value for magneto-elastic emission intensity of the sensor taken at, respectively, a first and second interrogation frequency. A change in mass or a change in material stiffness of the sensor due to the responsiveness, the viscosity and mass density of a fluid therearound, or the temperature, can be identified. The receiver, alternatively, measures a plurality of successive values for magneto-elastic emission intensity of the sensor taken over an operating range of successive interrogation frequencies to identify a value for the sensor's magneto-elastic resonant frequency (a fundamental frequency or harmonic thereof). Several sensors in an ordered array will provide a "package" of information.

30 Claims, 11 Drawing Sheets

U.S. PATENT DOCUMENTS

| | | |
|---|---|---|
| 5,083,112 A | 1/1992 | Piotrowski et al. .......... 340/572 |
| 5,130,697 A | 7/1992 | McGinn ...................... 340/551 |
| 5,348,761 A | 9/1994 | Mitter et al. ................. 427/101 |
| 5,499,015 A | 3/1996 | Winkler et al. ............. 340/551 |
| 5,508,203 A | 4/1996 | Fuller et al. ................. 436/149 |
| 5,514,337 A | 5/1996 | Groger et al. ............ 422/82.08 |
| 5,538,803 A | 7/1996 | Gambino et al. .... 428/694 TM |
| 5,552,778 A | 9/1996 | Schrott et al. .......... 340/825.34 |
| 5,554,974 A | 9/1996 | Brady et al. ................. 340/572 |
| 5,563,583 A | 10/1996 | Brady et al. ................. 340/572 |
| 5,565,847 A | 10/1996 | Gambino et al. ............ 340/572 |
| 5,597,534 A | 1/1997 | Kaiser ...................... 422/82.08 |
| 5,698,089 A | 12/1997 | Lewis et al. ................. 205/787 |
| 5,705,399 A | 1/1998 | Larue ......................... 436/501 |
| 5,754,110 A | 5/1998 | Appalucci et al. ........... 340/572 |
| 5,821,129 A | 10/1998 | Grimes et al. .............. 436/151 |
| 5,841,350 A | 11/1998 | Appalucci et al. .......... 340/572 |
| 5,859,587 A | 1/1999 | Alicot et al. ................. 340/572 |
| 5,981,297 A * | 11/1999 | Baselt ........................ 436/514 |
| 6,286,361 B1 * | 9/2001 | Jones et al. ................. 73/24.05 |

* cited by examiner

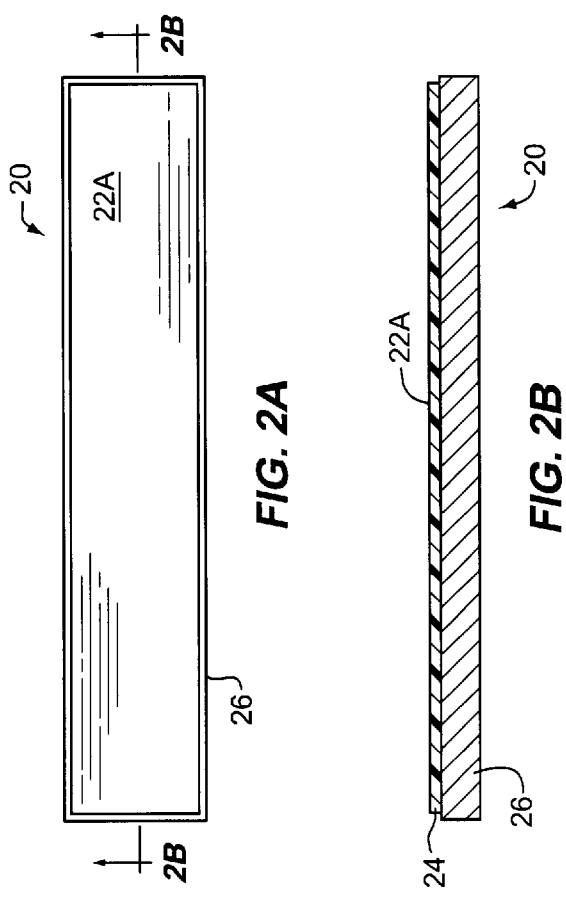
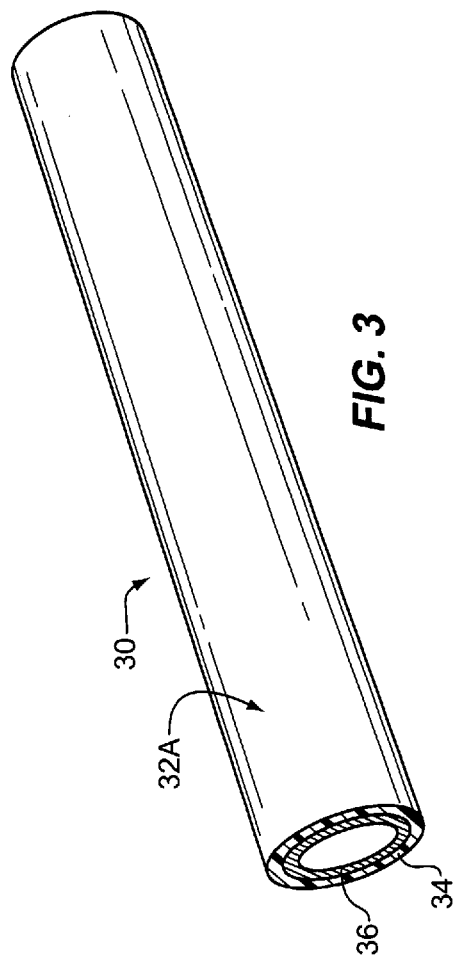
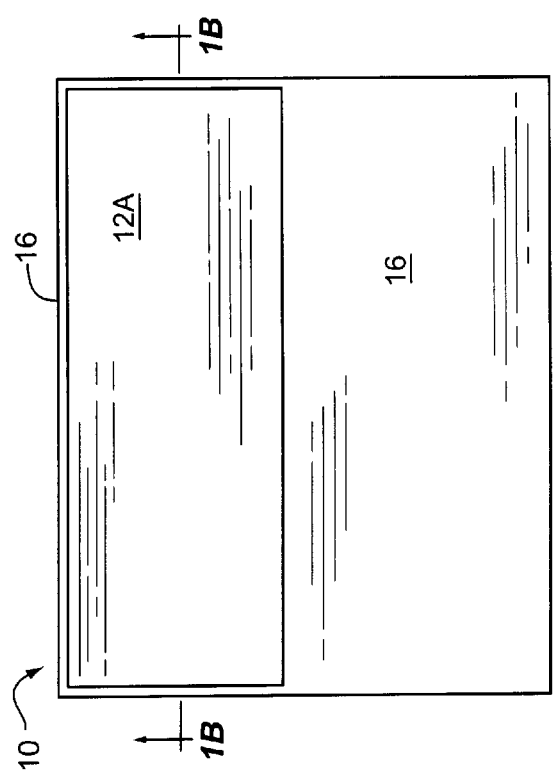

METHOD OF SENSING TEMPERATURE of an ENVIRONMENT

METHOD OF SENSING FLUID VISCOSITY

REMOTE MAGNETO-ELASTIC ANALYTE, VISCOSITY AND TEMPERATURE SENSING APPARATUS AND ASSOCIATED METHODS OF SENSING

The invention disclosed herein was produced as a result of work performed under a project funded, in part, by one or all of the following federal agencies: NASA, NSF, and NIH. As a result, the U.S. Government may have rights to the invention claimed herein.

BACKGROUND OF THE INVENTION

In general, the present invention relates to chemical telemetry using chemical sensing devices remotely located from associated pick-up and processing units for the sensing and monitoring of analytes, fluid properties such as viscosity and density, and temperature. More particularly, the invention relates to a novel remote analyte sensing apparatus, temperature sensing apparatus, and viscosity sensing apparatus, and associated new methods of sensing temperature of an environment, sensing viscosity, and sensing the presence, concentration, or absence of chemical elements and compounds (whether useful or unwanted/contaminating and in any of various states: liquid, gas, plasma, and solid), pH levels, germs (bacteria, virus, etc.), enzymes, antibodies, and so on in a number of environments such as biomedical applications (whether in vivo or in vitro), within medical test samples, food quality/inspection (whether measuring moisture within sealed packing or outside of packaging), monitoring of heavy metals found in water (groundwater, treated water, or wastewater flowing in natural waterways, canals, or pipes), and monitoring of solid or gas manufacturing waste, etc. The new sensing apparatus and method(s) provide information about an analyte and environment utilizing magneto-elastic emissions of a sensor, or several sensor structures.

Known chemical sensing technologies generally require the operation of complex, specifically tailored sensing units, electrically connected, to monitor a target analyte. For example, Groger et al. has a FIG. 4 with a chemically sensitive film 93 positioned between coils 92 and 94 (each of which has been wrapped around a ferrite core); a FIG. 5 with eddy current probes 21 formed by chemical deposition or chemically etching a copper clad printed circuit board (PCB) substrate 11 of a conductive polymer film of polypyrrole, polythiophene or polyaniline which may be deposited directly onto the inductor array or separated by spacers; and a FIG. 6 showing a spiral-wound inductor eddy current probe 13 with a thick film ferrite core 42 deposited on (or etched on) a PCB substrate 12. The Groger et al. probe design is incorporated into an instrument that has a digital signal processor (DDS) circuit. FIG. 9 illustrates that the probe 83 (such as that in FIG. 3 or 6) is in electrical connection with, and driven by, sinewave generator 80, preferably a direct digital signal generator, and an op amp 85 to produce a waveform output 86.

Kaiser illustrates a sensor 12, measurement circuit 10 and responder unit 16 coupled to a PCB 22 as an integrated circuit 24 (see FIGS. 1, 2A, and 2B), all contained in a housing 18. The integrated circuit 24 (FIG. 2A) is electrically connected to a sensor electrode 20 and reference electrode 21: The potential difference that develops between the electrodes 20 and 21 in relation to ion concentration, is measured to provide a pH level reading. In FIG. 2B, the sensor 12 of integrated circuit assembly 24 is a temperature sensor which is completely sealed within housing 18. FIGS. 3, 4, and 5 illustrate measurement circuit 10 embodiments: In 3 and 4, a voltage follower 44 outputs a signal proportional to the potential difference detected at sensor 12; FIG. 5 illustrates a familiar Wheatstone bridge with an AC generator 200 powered by an interrogation signal sent by interrogation unit 14. In operation (FIGS. 1 and 6), the RF transmitting and receiving circuitry 64 of interrogation unit 14, transmits an inquiry signal. Sometime thereafter, upon detecting its proper responder unit address, the responder unit 16 transmits data from the measurement circuit 10 back to interrogation unit circuitry 64.

Lewis et al. describes an analog of the mammalian olfactory system (i.e., electronic-nose) having chemiresistor elements micro-fabricated onto a micro-chip. Each sensor has at least first and second conductive leads electrically coupled to and separated by a chemically sensitive resistor (FIG. 4A-1). Each resistor has a plurality of alternating nonconductive and conductive regions transverse to the electrical path between the conductive leads. The chemiresistors are fabricated by blending a conductive material with a nonconductive organic polymer such that the electrically conductive path between the leads coupled to the resistor is interrupted by gaps of non-conductive organic polymer material. See, column 3, lines 38–50. Lewis et al. describes this as "electronic noses, for detecting the presence of an analyte in a fluid" (col. 8). An electronic smelling system according to Lewis et al. (col. 7) has sensor arrays in electrical communication with a measuring device for detecting resistance across each chemiresistor, a computer, a data structure of sensor array response profiles, and a comparison algorithm.

One of the applicants hereof, in conjunction with another, developed a magneto-chemical sensor comprised of a thin polymeric spacer layer made so that it swells in the presence of certain stimuli, bounded on each side by a magnetically soft thin film, as described in an article co-authored by the applicant entitled A Remotely Interrogatable Magnetochemical pH Sensor, IEEE Transactions on Magnetics, Vol. 33, No. 5, September 1997. When placed within a sinusoidal magnetic field the sensor generates a series of voltage spikes in suitably located detecting coils. The magnetic switching characteristics of the sensor are dependent upon the thickness of the sandwiched intervening polymeric spacer layer. The sandwiched "chemical transduction element" of this magnetism-based technology was made of a lightly crosslinked polymer designed to swell or shrink with changes in the concentration of the species to be sensed. The magnitude of each of the voltage spikes generated by the sensor is dependent upon how much the sandwiched spacer layer has swollen in response to the given stimuli. This sensor can be used with interrogation and detection electronics commonly used in magnetic anti-theft identification marker systems.

In a subsequent structurally-modified magnetochemical sensor developed by the applicants hereof, with others (A Remotely Interrogatable Sensor for Chemical Monitoring, IEEE Transactions on Magnetics, Vol. 34, No.4, July 1998), a thin film single or array of magnetostatically coupled magnetically soft ferromagnetic thin film structure(s) is adhered to a thin polymeric layer made so that it swells or shrinks in response to a chemical analyte. The sensor is placed within a sinusoidal magnetic field and the magnetization vector of the magnetically soft coupled sensor structures periodically reverses direction generating a magnetic flux that can be remotely detected as a series of voltage spikes in pick-up coils. The four-square array is of magnetically soft thin structures bonded to a polymeric base-substrate layer with acrylate acetate (SUPERGLUE®) and baked. When the swellable base swells (low pH): the distance between the square magnetically soft structures enlarges resulting in less coupling between these structures. If immersed in high pH: this base shrinks as does the distance between structures resulting in a larger voltage signal.

Anderson, III et al. discloses a marker 16 (FIG. 5) formed of a strip 18 of a magnetostrictive, ferromagnetic material adapted, when armed in its activated mode, to resonate mechanically at a frequency within the range of the incident magnetic field. A hard ferromagnetic element 44 disposed adjacent to the strip 18 is adapted, upon being magnetized, to magnetically bias the strip 18 and thereby arm it to resonate at that frequency. An oscillator provides an AC magnetic field within interrogation zone 12 to mechanically resonate a magnetostrictive strip 18, which has first been armed by a magnetized hard ferromagnetic element 44, upon exposure to this AC magnetic field. The sole object of Anderson, III et al. EAS marker is to detect the presence between coil units 22 and 24 (interrogation zone 12) of an "armed/activated" marker 16. In the event an activated marker 16 secured to a retail article is detected within zone 12, an alarm will sound. A deactivator system 38, electrically connected to a cash register, can be used to deactivate the marker. FIG. 3 graphically illustrates that, for the Anderson, III et al. marker, the voltage induced by mechanical energy exchange peaks (just over 12 volts) at $f_r$, the resonant frequency, and is a minimum at $f_a$ (anti-resonant frequency).

Humphrey and, another reference, Humphrey et al. disclose harmonic type electronic article surveillance (EAS) markers which include a thin strip or wire of magnetic material that responds to an alternativing interrogation signal by generating a signal pulse that is rich in high harmonics of the interrogation signal.

Winkler et al. relates to electronic article surveillance (EAS) anti-theft systems, which operate by detecting mechanical resonances of magnetostrictive elements made of amorphous metallic glass METGLAS® 2826 MB, to prevent or deter theft of merchandise from retail establishments. FIG. 8 illustrates a magnetomechanical system for detecting unauthorized passage through an interrogation zone of an article of merchandise. In response to an interrogation signal generated by energizing circuit 201, the interrogating coil 206 generates an interrogating magnetic field, which in turn excites the integrated marker portion 12 of the article of merchandise 10 into mechanical resonance. During the period that the circuit 202 is activated, and if an active marker is present in the interrogating magnetic field, such marker will generate in the receiver coil 207 a signal at the frequency of mechanical resonance of the marker. This signal is sensed by a receiver which responds to the sensed signal by generating a signal to an indicator to generate an alarm.

Copeland discloses an article surveillance system having two (first and second) diverse magnetic materials with diverse timewise responsivity to the magnetic field in the control zone. The first is a tag or marker material having principal responsivity to the magnetic field at or near the zero-crossover current of the time-varying signal; and the second is a shielding material with a principal responsivity to the magnetic field at or near the peaks of the positive and negative excursions of the time-varying signal (i.e., selected to function as a shield). A method aspect is also explained.

Schrott, et al. describes a multibit bimorph magnetic ID tag for attachment to, and identification of, an object. The tag has one or more bimorphs comprised of a thin strip of a magnetostrictive material attached to a thicker bar 21 of hard magnetic material. A shipping pallet, package, or product is tagged with the bimorph for later product identification. The Schrott, et al. ID tag is excited using either magnetic or acoustic fields (ranging in frequency up to 50 to 100 kHz, and preferably 5–50 kHz) tuned to the resonance of the bimorph tags. The bar 21 of hard magnetic material of the bimorph cantilever is several times (e.g. 5) thicker, for the same length, than the magnetostrictive strip, in order to have the bimorph vibrate at frequencies determined by the bar dimensions. The excitation induces strain in the bimorph which causes mechanical vibrations in the bimorph that are sensed acoustically or magnetically, giving rise to a predetermined code tied directly to whether the ID tag is resonating at the interrogation frequency (ON), or it is not (OFF). A device for detecting the output of the tag, along with a device 8 for decoding the output from the detecting means thereby, are also needed. Schrott et al. indicates that a multibit tag could be programmed to generate a binary or other suitable code. In the binary code case, a certain frequency of an array of cantilevers can be assigned a value of "zero" or "one" and, if absent, it can take the opposite value. The Schrott, et al. ID tag is limited to coded (zeros and ones) identification of the object. If, in operation, a Schrott, et al. ID tag's resonant frequency (predetermined by size/materials) is not "hit" during interrogation due to some unexpected event/external factor (such as, its resonant frequency is changed due to a temperature swing, or due to reaction of the ID tag with a surrounding fluid), no response will be detected and an incorrect output code will result, thus, destroying the Schrott, et al. ID tag's function.

As one can appreciate, unlike the instant invention, known electrical system chemical sensors available for use are dependent upon direct electrical connection between the sensing unit and an input AC-energy or sinewave generator, and output measurement circuitry having an associated directly-connected computer processor. Although chemical analysis is being done using laser reflection, such laser analysis requires that a fiber optic cable or light beam enter the environment being tested; making laser analysis difficult (if not impossible) within opaque packaging or piping, in vivo, and so on, where no line-of-sight for the laser beam can be reliably maintained. These known sensors have been designed for specifically-targeted test environments. The particular magnetochemical sensors (described above, see A Remotely Interrogatable Magnetochemical pH Sensor, *IEEE Transactions on Magnetics*, Vol. 33, No. 5, September 1997) developed in collaboration with the applicant hereof, have been designed with a crosslinked polymer chemical transduction element adhered to a magnetically soft ferromagentic thin film structure to specifically respond to a surrounding sinusoidal magnetic field by detecting changes in magnetic flux (as voltage spikes). And, known magnetic markers developed for use in EAS simply register the presence or absence of the magnetic marker, as sensed within a region, based upon the EAS marker's response to a magnetic field produced by a magnetic field transmitter. Furthermore, many of the currently available chemical sensor systems rely on proper orientation of the sensor within the interrogation field. This is undesirable, as it is often very difficult to guarantee a particular sensor orientation within most test environments (example, in vivo testing).

Viscosity, defined as the resistance that a gaseous or liquid (i.e., a fluid) system offers to flow when it is subjected to a shear stress, is generally measured by cumbersome meters.

Mathematically, the shear stress (τ) of a fluid near a wall is given by:

$$\tau = \mu \frac{dV}{dy} \quad [1]$$

where μ is the dynamic viscosity and dV/dy is the time rate of strain (also called the velocity gradient). As one can see, dynamic viscosity μ (having units N·s/m$^2$) is the ratio of shear stress to velocity gradient. Measuring viscosity, especially of a fluid in motion, is no simple task.

Therefore, a versatile robust sensor apparatus and method are needed for obtaining information about an analyte or an environment (including one with a fluid therewithin) through remote query, without direct electrical hard-wire connection and without the need to ensure the sensor's orientation in order to provide such information, in various diverse test samples/environments.

The new compact analyte, temperature, and viscosity sensing apparatuses, and associated methods of sensing, described herein, are designed for operation within a wide range of tests and testing environments whether one-time, periodic, or continuous on-going monitoring of a particular analyte or environment is desired. The innovative sensing apparatus and method use a base magnetostrictive element to which a chemically, thermally, or frictionally responsive layer/element may be adhered to create a unique analyte recognition, temperature or viscosity sensing structure and technique that can utilize either: (a) a ratio of magneto-elastic energy emission measurements of the sensor structure taken at two different magneto-elastic listening frequencies (preferably around a fundamental or harmonic resonant frequency), or (b) at least two successive magneto-elastic emission intensity values taken over a range of successive interrogation frequencies (preferably including a fundamental or harmonic resonant frequency), to identify a fluid viscosity or temperature, or detect the presence, absence, and/or measure minute, and larger, amounts of an analyte in gas, plasma, liquid, or solid phase. This being done without requiring sophisticated equipment and without taking up a great deal of space. Furthermore, this new sensor structure can be installed/positioned and removed with relative ease and without substantial disruption of the test sample or test environment. If need be, the sensor may be fabricated as a micro-circuit for use in vitro, in vivo, within small-sized sealed packaging or medical test samples (e.g., a test tube), and so on. A micro-sensor can be used where space is limited and/or it is desired that the tiny sensor be positioned further into the interior of the sample or environment being tested/monitored. And, whether or not built on a larger scale, the novel sensor can be used for sensing within buildings or other open space to measure contaminant gas, in waterways to measure heavy-metal contamination, and so on.

Simply defined, "magnetostriction" is the phenomena whereby a material will change shape (dimensions) in the presence of an external magnetic field. This effect is brought about by the reordering of the magnetic dipoles within the material. Since the atoms in a magnetostrictive material are not, for all practical purposes, perfectly spherical (they're shaped more like tiny ellipsoids) the reordering of the dipoles causes an elongation (or contraction depending on the mode of reorientation) of the lattice which leads to a macroscopic shape change in the material. There is a "reverse magnetostrictive effect", called the Villari effect: When an external stress is applied to a magnetostrictive material, a strain develops within the material which induces a surrounding magnetic field. Known magnetostrictive materials include alloys of iron (Fe), cobalt (Co), samarium (Sm), yttrium (Y), gadolinium (Gd), terbium (TB), and dysprosium (Dy).

The new analyte, temperature, and viscosity sensing apparatuses and methods were developed to utilize space more efficiently while at the same time provide sufficient sensitivity. As can be appreciated, in the spirit and scope of these design goals and as described further, the sensor structures can be fabricated from micro-components or can be built on a larger scale and formed into many different shapes and layers; and several such sensors can be incorporated into an array to provide a package of sensing information.

SUMMARY OF THE INVENTION

It is a primary object of this invention to provide apparatuses and associated methods for detecting the presence, absence, and/or measuring the amount of an analyte, as well as sensing the temperature of an environment (whether or not a fluid is within the environment) and sensing fluid viscosity, mass density or other such property. A sensing structure (sensor) is used that has a base magnetostrictive element to which a chemically, thermally, or frictionally responsive layer/element (as the case may be) may be adhered. It is also an object of this invention that such apparatuses and methods utilize either: (a) a ratio of magneto-elastic energy emission measurements of the sensor structure taken at two different magneto-elastic listening frequencies, or (b) at least two successive magneto-elastic emission intensity values taken over a range of successive interrogation frequencies, to perform the sensing/detecting. It is also an object of this invention to provide such a sensing structure that needs no direct hard-wire connection to its field generating coil or magneto-elastic emission receiving coil, but rather, is remotely located for sensing.

The advantages of providing the new analyte and temperature sensing apparatuses and associated new methods, as described herein, are as follows:

(a) The invention can be used for one-time (whether disposable) operation, periodic, or continuous on-going monitoring of a particular analyte or environment;

(b) Versatility—The invention can be used for operation within a wide range of testing environments such as biomedical applications (whether in vivo or in vitro), within medical test samples, food quality/inspection (within or outside of sealed packing), monitoring of contaminants in water (groundwater, treated water, or wastewater flowing in natural waterways, canals, or pipes), and monitoring of solid or gas manufacturing waste;

(c) Simplicity of use—The new sensor structure can be installed/positioned and removed with relative ease and without substantial disruption of a test sample/environment;

(d) Structural design flexibility—the sensor may be formed into many different shapes and may be fabricated as a micro-circuit for use where space is limited and/or the tiny sensor must be positioned further into the interior of a sample or environment being tested/monitored;

(e) Structural design for sensing speed—If a layer of chemically or thermally responsive material is adhered to the magnetostrictive base, that layer can be shaped to maximize the speed at which the material responds, allowing the sensor to provide useful information at a faster rate;

(f) Several sensors may be positioned, each at a different location within a large test environment, to sample each of the different locations, simultaneously or sequentially;

(g) Several sensors may be incorporated into an array to provide a package of sensing information about an environment, such as, analyte composition, a fluid viscosity or mass density measurement, and temperature of the environment in which the analyte and fluid are found;

(h) Receiving unit design flexibility—One unit may be built with the capacity to receive acoustic emissions (elastic nonelectromagnetic waves that can have a frequency up into the gigahertz, GHz, range) as well as electromagnetic emissions emanating from the sensor, or separate acoustic wave and electromagnetic wave receiving units may be used;

(i) Apparatus design simplicity—Reducing the number and size of components required to build an analyte, viscosity (or other fluid property), or temperature sensing apparatus can reduce overall fabrication costs and add to ease of operation; and (j) Sensor materials and size can be chosen to make one-time, disposable use economically feasible.

Briefly described, the invention includes an analyte sensing apparatus for operative arrangement within a time-varying magnetic field, comprising a sensor having an outer surface of a material that is chemically responsive to the analyte, adhered to a base magnetostrictive element, and a receiver to measure a first and second value for magneto-elastic emission intensity of the sensor taken at, respectively, a first and second interrogation frequency. A change in mass, if any, of the sensor (or a change in its material stiffness) due to the chemical responsiveness is identified using a ratio of the first and second values. The first interrogation frequency is preferably less than the sensor's magneto-elastic resonant frequency (or harmonic thereof) by an interval ($\Delta f$) from the magneto-elastic resonant frequency, and the second interrogation frequency is preferably greater than the resonant frequency (or harmonic thereof) by approximately the interval ($\Delta f$); $\Delta f$ may be a value between 0.001% and 20% (and, perhaps, up to 40%) times the resonant frequency $f_o$ (or a harmonic).

Also described is an analyte sensing apparatus, comprising this sensor and a receiver to measure a plurality of successive values for magneto-elastic emission intensity of the sensor taken over an operating range of successive interrogation frequencies to identify a magneto-elastic resonant frequency (or harmonic thereof) value for the sensor; whereby a change in mass, if any, of this sensor due to the chemical responsiveness is identified by using the magneto-elastic resonant frequency value. The resonant frequency value identified generally corresponds with a relative maximum of the successive values for emission intensity measured. This range of successive interrogation frequencies could be chosen as a range between 79% and 121% of the resonant frequency (or harmonic) for the sensor.

Also characterized herein, is a temperature sensing apparatus for operative arrangement within an environment having a time-varying magnetic field. This apparatus comprises: a sensor having a base magnetostrictive element; and a receiver to measure a first and second value for magneto-elastic emission intensity of the sensor taken at, respectively, a first and second interrogation frequency; whereby temperature of the environment is identified using a ratio of the first and second values. As before, the first interrogation frequency is preferably less than the sensor's magneto-elastic resonant frequency (or harmonic thereof) by an interval ($\Delta f$), and the second interrogation frequency is preferably greater than the resonant frequency (or harmonic thereof). A pre-correlation made between a series of emission intensity ratio values taken for the sensor and a corresponding series of temperature values for the sensor, is used for the identification of the environment's temperature. An outer surface of a material (such as a polymer) that is thermally responsive to the environment can be adhered to the base element.

Also characterized herein, is a temperature sensing apparatus comprising: a sensor having a base magnetostrictive element; and a receiver to measure a plurality of successive values for magneto-elastic emission intensity of the sensor taken over an operating range of successive interrogation frequencies to identify a magneto-elastic resonant frequency value for the sensor; whereby temperature of the environment is identified by using the resonant frequency value.

Additionally, the temperature sensing apparatuses may incorporate a sensor with a thermally responsive thin outer layer having a value for coefficient of thermal expansion that is greater than a coefficient of thermal expansion value for its base element. The base element may be sandwiched between two such layers (e.g., out of antimonial lead or zinc).

Also characterized herein, is an apparatus for sensing at least one property of a fluid for operative arrangement within a time-varying magnetic field, comprising: a sensor having a base magnetostrictive element, and a receiver to measure either (a) a first and second value for magneto-elastic emission intensity of the sensor taken at, respectively, a first and second interrogation frequency, whereby the fluid property is identified using a ratio of these first and second values, or (b) a plurality of successive values for magneto-elastic emission intensity of the sensor taken over an operating range of successive interrogation frequencies to identify a magneto-elastic resonant frequency value for the sensor, whereby the fluid property is identified by using this magneto-elastic resonant frequency value. As before, the first interrogation frequency is preferably less than the sensor's magneto-elastic resonant frequency (or harmonic thereof) by an interval ($\Delta f$), and the second interrogation frequency is preferably greater than the resonant frequency (or harmonic thereof). The fluid property sensor, operating as a viscosity sensor, may further comprise an outer surface that is frictionally responsive to the fluid being sensed; and a fixture to slidably retain the sensor can be incorporated with this viscosity sensing apparatus.

The magneto-elastic emission may be an acoustic emission, an electromagnetic emission, or other detectable wave type emitted by the sensor. And, the type of receiver used (such as an electroacoustic device containing a transducer or an electromagnetic pick-up coil) will depend upon the type of magneto-elastic emission being received. If electromagnetic emission intensity is measured by the receiver, one may choose to perform such measurement after the time-varying magnetic interrogation field has been turned off. The magnetostrictive element can be made of an alloy of an element selected from: iron, cobalt, samarium, yttrium, gadolinium, terbium, dysprosium, and so on. For the analyte and viscosity sensors, it is preferred that an alloy is chosen having material properties that remain generally unchanged over a preselected range of operating temperatures.

There are additional features that further distinguish the apparatuses of the invention from known sensing system designs. The chemically responsive outer surface can be that of many different types of materials, such as (note that the particular mechanism of chemical responsiveness is not critical): A chemically receptive polymer layer having a plurality of microspheres; a chemically receptive porous polymer layer (into which at least a portion of the analyte can diffuse); a sorbent polymer film selected from the group of a poly(isobutylene), ethylene-propylene rubber, poly (isoprene), and poly(butadiene) film; an outer polymer hydrogel monolayer reactive to electrostatic forces of subatomic particles within the analyte; a chemically receptive polymer layer (from which there is a loss of matter); a zeolite layer which can interact with at least a portion of subatomic particles in the analyte to cause a gain in mass of the zeolite layer; and so on. The frictionally responsive layer can be that of a layer of latex, and such, to increase surface roughness.

Furthermore, a magnetizable magnetically hard element can be positioned in proximity to the analyte, viscosity, or temperature sensor to act as an ON-OFF switch; or, such a magnetized (activated) magnetically hard element could be positioned to provide a DC bias magnetic field superimposed onto the time-varying field. In operation the ON-OFF switch, once activated to support an external stray magnetic field, would reversibly turn the sensor structure off. In the event a "package" of different types of sensing information about one environment is sought, more than one sensor may be maintained in an ordered array, for example, by being organized to extend along or contained within chambers of a support member. Each sensor within the array may have a distinct operating range, allowing the receiver to distinguish emissions received from each separate sensor. Thus, the separate types of sensing information can be obtained, tracked and computed. A magnetically hard element can, likewise, be organized along or within the support member (although it need not be attached thereto) in proximity to a dedicated sensor structure for activation to contribute a DC bias field to that surrounding the sensor.

The invention also includes a method of sensing an analyte with a sensor having a chemically responsive outer surface adhered to a base magnetostrictive element, the sensor having a magneto-elastic resonant frequency, comprising the steps of: applying a time-varying magnetic field; measuring a first and second value for magneto-elastic emission intensity of the sensor with a receiver operating at, respectively, a first and second interrogation frequency; and using a ratio of the first and second values to identify a change in mass, if any, of the sensor due to the chemical responsiveness. As before, the first interrogation frequency is preferably less than the sensor's magneto-elastic resonant frequency (or harmonic thereof) by an interval ($\Delta f$) from the magneto-elastic resonant frequency, and the second interrogation frequency is preferably greater than the resonant frequency (or harmonic thereof) by an interval ($\Delta f$): $\Delta f$ can be a value between 0.00% and 20% (and up to 40%) times the resonant frequency $f_0$ (or a harmonic). The method can also include, prior to the step of using a ratio, the step of pre-correlating a series of emission intensity ratio values taken for the sensor and a corresponding series of mass change values for the sensor (this step of pre-correlating can be used to identify a change in mass, if any). If there is no mass change, a change in material stiffness of the sensor due to the chemical responsiveness may be identified. To further accomplish the sensing of the analyte, the step of applying a known relationship between the change in mass (or change in material stiffness, as the case may be) and the analyte (or material property thereof), can be included.

Also characterized herein, is a method of sensing an analyte with a sensor having a chemically responsive outer surface adhered to a base magnetostrictive element, comprising the steps of: applying a time-varying magnetic field; measuring a plurality of successive values for magneto-elastic emission intensity of the sensor with a receiver operating over a range of successive interrogation frequencies to identify a magneto-elastic resonant frequency value for the sensor; pre-correlating a series of resonant frequency values taken for the sensor and a corresponding series of mass change values for the sensor; and using the magneto-elastic resonant frequency value identified and the step of pre-correlating to identify a change in mass, if any, of the sensor due to the chemical responsiveness. This range of successive interrogation frequencies could be chosen as a range somewhere between 79% and 121% of the resonant frequency for the sensor.

Additional novel methods of the invention are characterized herein. One being a method of sensing a temperature of an environment with a sensor having a base magnetostrictive element, comprising the steps of: applying a time-varying magnetic field; measuring a first and second value for magneto-elastic emission intensity of the sensor with a receiver operating at, respectively, a first and second interrogation frequency; and using a ratio of the first and second values to identify the temperature. Another method of sensing a temperature of an environment with a sensor having a base magnetostrictive element, includes the steps of: applying a time-varying magnetic field; measuring a plurality of successive values for magneto-elastic emission intensity of the sensor with a receiver operating over a range of successive interrogation frequencies to identify a magneto-elastic resonant frequency value for the sensor; pre-correlating a series of resonant frequency values taken for the sensor and a corresponding series of temperature values for the sensor; and using the magneto-elastic resonant frequency value identified and the step of pre-correlating to identify the temperature.

Further characterizations of the method of the invention, include a method of sensing at least one property (such as viscosity or mass density) of a fluid with a sensor having a base magnetostrictive element, comprising the steps of applying a time-varying magnetic field, and either:

(a) measuring a first and second value for magneto-elastic emission intensity of the sensor with a receiver operating at, respectively, a first and second interrogation frequency, and using a ratio of the first and second values to identify the fluid's property; or (b) measuring a plurality of successive values for magneto-elastic emission intensity of the sensor with a receiver operating over a range of successive interrogation frequencies to identify a magneto-elastic resonant frequency (or harmonic thereof) value for the sensor, pre-correlating a series of resonant frequency values taken for the sensor and a corresponding series of viscosity values for the sensor, and using the resonant frequency (or harmonic) value and the pre-correlation to identify the property.

There are additional features that further distinguish the methods of the invention from known sensing system and method designs. In the event a "package" of different types of sensing information about one environment is sought, one can add the step of measuring a third and fourth value for magneto-elastic emission intensity of a second sensor with the receiver operating at, respectively, a third and fourth interrogation frequency; or one could add the step of measuring a second plurality of successive values for magneto-elastic emission intensity of a second sensor with said receiver operating over a second range of successive interrogation frequencies to identify a magneto-elastic resonant frequency value for the second sensor. If at least three types of sensing information is sought, one could further add the step of measuring a third plurality of successive values for magneto-elastic emission intensity of a third sensor with the receiver operating over a third range of successive interrogation frequencies to identify a magneto-elastic resonant frequency value for the third sensor, and so on. Each of the sensors may extend along, or be contained within a chamber of, a support member in an ordered array, or each could be immersed for free independent movement throughout the environment. A dedicated DC bias magnetic field may be desirable for each, or any one of, the sensors in the array.

BRIEF DESCRIPTION OF THE DRAWINGS

The invention will be more particularly described by referencing the accompanying drawings of the preferred embodiments, in which like numerals designate like parts.

FIG. 1A is a top plan view of a rectangular-shaped sensor structure 10 of the invention having an outer surface (here, comprising surface 12a of either a chemically, thermally, or frictionally responsive layer shown extending over only a portion of a magnetostrictive base element 16) chemically responsive to the analyte of interest. This outer surface can substantially cover the base 16 as shown in FIG. 2A.

FIG. 1B is a sectional view taken along 1B—1B of FIG. 1A illustrating one preferred way to adhere outer surface 12a of layer 14a to base 16 with an adhesive layer 18.

FIG. 2A is a top plan view of a preferred analyte sensor 20, shaped in the form of a ribbon/strip, with an outer surface 22a substantially covering a magnetostrictive base 26.

FIG. 2B is a sectional view taken along 2B—2B of FIG. 2A illustrating a generally planar outer surface 22a of layer 24 adhered to base 26.

FIG. 3 is an isometric view of an alternate analyte sensor 30, cylindrically-shaped, having an outer surface 32a of a layer 34 covering a magnetostrictive base 36.

DETAILED DESCRIPTION OF THE PREFERRED EMBODIMENTS

Figure 4:
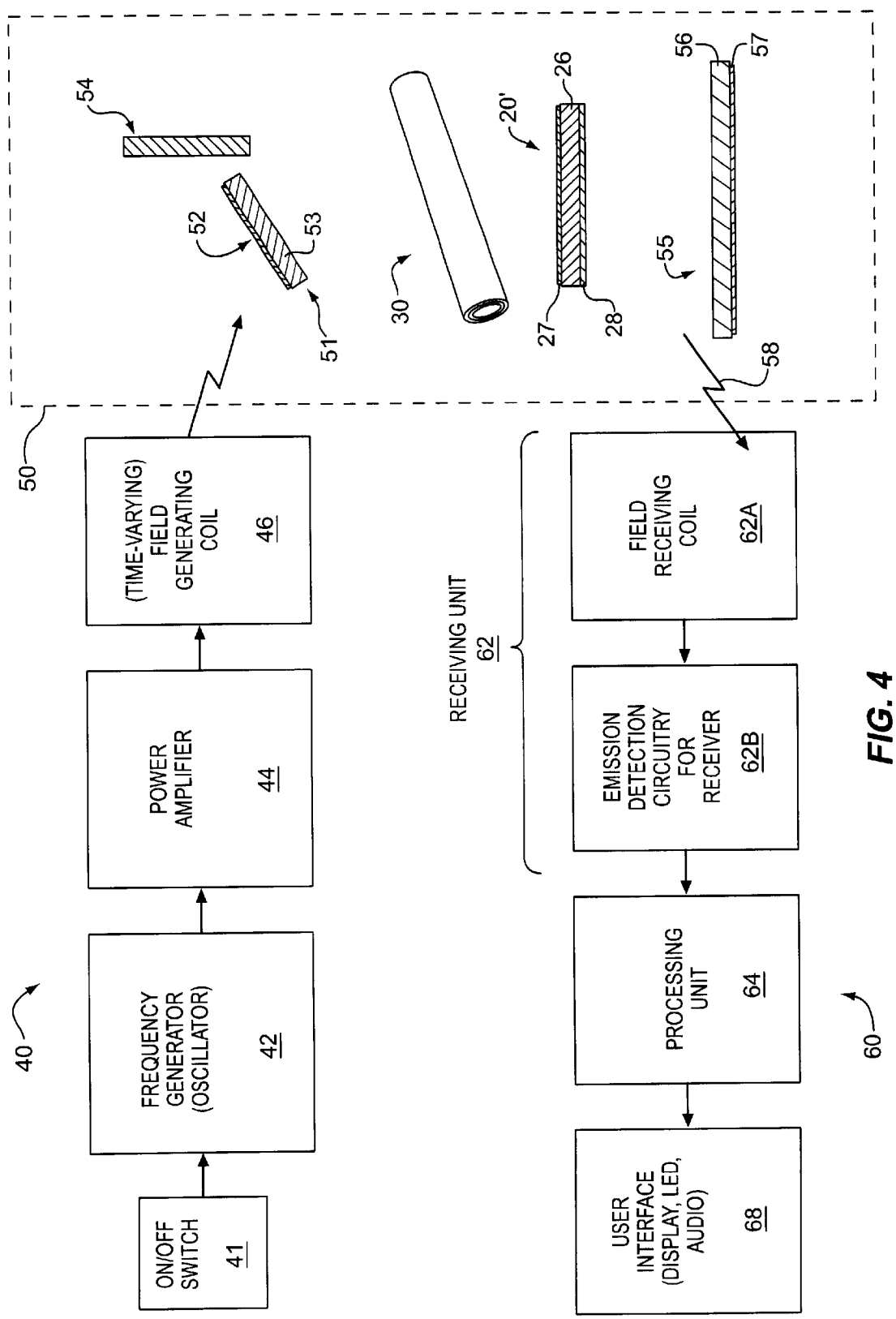
FIG. 4 illustrates preferred analyte, viscosity, and temperature sensing apparatuses of the invention, in schematic-block diagram form. Sensor structures similar to those depicted in FIGS. 1A, 2A, and 3 are shown positioned within an environment defined by boundary 50.

The rectangular-shaped analyte sensor structure 10 is illustrated in FIGS. 1A and 1B with an outer surface 12a adhered over a portion of base element 16. The outer surface shown at 12a is chosen for a desired chemical responsiveness to the analyte (or a chosen property thereof) in question, for a desired frictional responsiveness to a fluid if measuring viscosity therefor, or for a desired thermal responsiveness to temperature of an environment in question. The outer surface (such as at 12a or 22a in FIG. 2B) may cover substantially the whole of a magnetostrictive base element by suitable means (depending upon the material chosen for surfaces 12a or 22a) such as sputtering, chemical deposition, application in liquid or gel form that is dried/evaporated or heated/cooled, as the case may be. Alternatively, outer layer 14a may be adhered to base 16 with a thin adhesive layer (FIG. 1B at 18) sandwiched between, and compatible with, chemically, frictionally, or thermally responsive layer 14a and base magnetostrictive element 16. Outer surface 12a need not cover the whole of base element 16, but rather, cover only that portion of base 16 necessary to produce a desired emission response when subject to a time-varying magnetic field. An outer surface 12a need not be planar as shown, but may take on any respective shape into which base 16 has been formed (such as the cylindrical base 36 shown in FIG. 3).

FIG. 1B is a sectional view of an additional layer 19 which may also be chemically, frictionally, or thermally responsive to the analyte or environment temperature, or may be of a magnetically hard material (MHM) also adhered to sensor structure 10. Such a MHM layer could be used to operate as an ON-OFF switch capable of remote activation as follows: The MHM 19 is initially demagnetized with only a minimal stray magnetic field so as not to interfere with sensor 10 operation. To turn sensor 10 OFF, the MHM can be exposed to a large DC electromagnetic field, such as that emitted by a magnet, which magnetizes/activates the MHM so that it supports a large external stray magnetic field. The MHM layer may be designed so that the stray field of an activated MHM is either larger than the interrogating time-varying magnetic field (whereby the sensor 10 effectively no longer responds to the interrogating time-varying field), or the activated MHM can act to bias the domain structure of the magnetostrictive element 16 (i.e., that region within which magnetic moments are uniformly arrayed) such that the resonant frequency of sensor 10 is no longer within operating range for the receiving unit (62 in FIG. 4). Sensor 10 can be remotely reactivated by demagnetizing the MHM layer by exposing it to a time-varying, gradually decreasing magnetic field the initial amplitude of which is greater than the MHM's coercive force.

One can readily appreciate the flexibility of the novel sensor design of the invention from the different structures illustrated at 20 and 30 in FIGS. 2A, 2B, and 3. Sensor 20 in FIGS. 2A and 2B is elongated in shape with a correspondingly shaped generally planar outer surface 22a of layer 24 which, like surface 12a in FIG. 1A, is preferably chosen for its selective chemical responsiveness to the analyte of interest (whether or not an ionic solution or gas), for its frictional responsiveness to a fluid (to roughen up the surface), or for its thermal responsiveness to temperature of an environment within which the sensor 20 has been positioned. Cylindrically-shaped structure 30 has a correspondingly shaped outer surface 32a of a layer 34. Sensors 10, 20, 30 may be sized as shown (several centimeters in length and width), may be built on a smaller scale (on the order of several millimeters in length and width), or may be fabricated as tiny micro-chip type elements using known integrated circuit (IC) fabrication etching, thin-film depositing, and cutting techniques. As the size decreases, the resonant frequency at which the sensor structure will emit waves gets higher (up to the GHz-range). Sensor structures (such as those at 10, 20, 30) need not have a rectangular or square periphery as shown: The sensor of the invention may be circular, oval, triangular, hexagonal, etc., in shape (peripheral shape may be important in the event a chosen sensor fabrication technique or a chosen magneto-elastic emission dictates).

The responsive layer (labeled 14a, 24, 34 in FIGS. 1B, 2B, and 3, respectively) may be made of many different suitable materials. The layer (14a, 24, 34), for example, may be made of a chemically receptive polymer that has microspheres (also called microbeads) capable of absorbing particulate matter (e.g., a sub-atomic particle such as a proton) in the analyte. One implementation of this is to prepare monolayers of lightly crosslinked derivatized polystryene microspheres having diameters on the order of 0.3 to 0.5 micometers. This is done by dispersion polymerization of vinylbenzyl chloride with ca. 2 mole-% divinylbenzene as the crosslinker. The chloromethyl group is aminated to introduce an amine group. This polymer swells upon protonation at low pH: Its microspheres swell individually, tending to minimize mechanical stresses on the polymer, thus, reducing cracking of the layer and delamination from base element 16. This implementation may be used for sensing a pH level of the analyte.

Another suitable material for the responsive layer(s) shown at 14a, 24, 34, is the pH sensitive chemical transduction spacer layer made of a polyacrylate polymer, such as a lightly crosslinked 2-(dimethylamino)ethyl methacrylate (DMAEMA), which is described in the scientific article A Remotely Interrogatable Magnetochemical pH Sensor, *IEEE Transactions on Magnetics,* Vol. 33, No. 5, September 1997 (cited above), developed in collaboration with the applicant hereof. Polyacrylate polymers are known to be hydophilic and, therefore, swell in water. Thus, the polymer network is permeable to aqueous analytes. Furthermore, it was identified in this article that thin films of polystyrene will swell in the presence of toluene and that polyhydroxyethyl methacrylate swells as a function of analyte moisture content (humidity). Any of these materials are suitable, here.

Hydrogels are crosslinked hydrophilic polymers which swell upon contact with moisture by reacting to the electrostatic forces of sub-atomic particles. Examples of synthetic hydrogels include: contact lenses and polymerized hydroxyethylmethacrylate (HEMA). N. F. Sheppard. Jr. et al. Microfabricated conductimetric pH sensor, Sensors and Actuators B vol. 28 (1995) 95–102 used a copolymerized HEMA with 2-(dimethyl-amino)ethyl methacrylate (DMAEMA), which introduces an amine group onto the polymer backbone, in their conductimetric pH sensor. Here, a lightly crosslinked polyHEMA-co-DMAEMA could be used since it swells at low pH when the amine group is protonated.

A chemically receptive porous layer (14a, 24, 34) into which the analyte can diffuse may be advantageous (such as by the transport of mass, in the form of discrete atoms, through the lattice of a crystalline solid); or one might incorporate an outer diffusion barrier (a porous barrier through which gaseous mixtures are passed for enrichment of the lighter-molecular-weight constituent of the diffusate). As shown in FIG. 1B, to speed up chemical response time, the outer surface is preferably of a thin layer of generally uniform thickness. It may be desirable, depending upon desired emission, to adhere the responsive surface over one or more small areas of the base element. Another material option for the responsive layer is a sorbant polymer film capable of vapor diffusion, selected from a group of sorbant polymer film materials identified in J. Grate, M. Abraham, Solubility interactions and the design of chemically selective sorbent coatings for chemical sensors and arrays, Sensors and Actuators B, vol. 3 (1991) 85–111, to include at least: poly(isobutylene), ethylene-propylene rubber, poly (isoprene), and poly(butadiene).

Other materials with chemical response mechanisms that make them suitable for use as the responsive layer of the instant invention (see FIGS. 1B, 2B, and 3 at 14a, 24, 34), include the following: (1) a hydrogel having boronate-containing polymer complexes that swell due to diffusion of ion species upon chemical responsiveness when in contact with glucose to sense glucose (blood sugar) concentration changes (as identified by A. Kikuchi et al., Glucose-Sensing Electrode Coated with Polymer Complex Gel Containing Phenyl-boronic Acid, Anal. Chem., vol. 68, pp.823–828, 1996; (2) a material capable of loss of particulate matter (such as a sub-atomic particle/proton) when interacting with the analyte; (3) a polymer capable of molecular interaction with, by-way-of absorption, the analyte to change the mass of the layer; and (4) zeolite (a clay-like structure that exhibits the behavior of a molecular sieve or filter—a crystalline compound), which "filters" carbon-rich gases flowing over the layer, causing a change in mass of the layer. The outer surface may also be that of a material (such as a polymer) that is thermally responsive to the environment within which the sensor has been positioned. One suitable material is a thermally-sensitive elastomer (or the "thermosensitive rubbery polymer" described by Y. Nagasaki et al. in the scientific article New Thermosensitive Rubbery Polymers. Synthesis of Poly (siloxyethylene glycol), Macromolecules 1996, 29, 5859–5863) which responds by thermo-chemical reaction with the intent of causing material swelling and a corresponding mass change in the layer, and/or change in material stiffness of the layer. Thermochemical reactions include those chemical reactions accompanied by a heat change (whether exothermic or endothermic), and perhaps also a change in state.

A novel temperature sensing apparatus of the invention may incorporate a sensor (such as those represented at 10, 20, 30 in FIGS. 1A–B, 2A–B, and 3) with a thermally responsive thin outer layer (represented at 14a, 19, 24, and 34) having a value for its coefficient of thermal expansion (CTE) that is greater than a coefficient of thermal expansion value for the associated base element (represented at 16, 26, and 36). The coefficient of thermal expansion of a material in solid, liquid, or gas phase is defined as: the increment in volume of a unit volume of the material for a rise of 1-degree temperature when the material is held at constant pressure. By way of example, a layer 16, 26, 36 of antimonial lead having a CTE value of about $28 \times 10^{-6}$/degree kelvin composed of 96% lead (Pb) and 4% antimony (Sb), or of Zinc having a CTE value of about $31 \times 10^{-6}$/degree kelvin, may be sputtered, evaporated, or chemically deposited using known techniques onto a magnetostrictive base made of an iron (Fe) and cobalt (Co) alloy which has a CTE value of about $12 \times 10^{-6}$/degree kelvin. In this example, for a given series of unit variations in temperature (degree kelvin), the thermally responsive layer will change size at a "faster rate" in response to the rise or fall in temperature than will an associated magnetostrictive base element. This phenomena results in placing the sensor structure under internal tensile stress, which in turn, changes the sensor's magneto-elastic resonant frequency.

A magnetostrictive base element, having no thermally responsive outer layer, placed within an environment will react to temperature variations as follows: A change in temperature of the environment will change the Young's modulus of elasticity of an element, resulting in a corresponding change in the resonant frequency of the element. However, by adding a thermally responsive layer having the characteristics described above (i.e., the CTE for the responsive material layer is greater than the CTE for the base), temperature sensitivity of the unique temperature sensor of the invention is more-easily adjustable. One just chooses a different thermally responsive material for adhesion to the base element to change the sensor's temperature sensitivity.

It may be desirable to add a layer of a material, such as a latex, over a portion (or substantially the whole) of a base magnetostrictive element to increase the surface roughness of the sensor when incorporated within a novel fluid viscosity sensing apparatus or method of the invention. As mentioned, viscosity is defined as the resistance that a fluid system offers to flow when it is subjected to a shear stress. Increasing surface roughness of a viscosity sensing structure of the invention heightens its sensitivity to changes in viscosity. When measuring a fluid with a low viscosity, such as water ($H_2O$), its is preferred that the sensor's outer surface be relatively rough; whereas the viscosity of a highly viscous fluid can be measured using a magnetostrictive element with its relatively smooth outer surface (no additional frictionally responsive, rough outer surface needs to be added).

Turning to the base element shown at 16, 26, and 36 of sensors 10, 20, and 30, respective in FIGS. 1A–B, 2A–B, and 3, suitable alloys, known for their magnetostrictive properties (as identified above) include: iron (Fe), cobalt (Co), samarium (Sm), yttrium (Y), gadolinium (Gd), terbium (TB), and dysprosium (Dy). We turn, by way of example, to ferromagnetic materials which are inherently magnetostrictive. A piece of ferromagnetic material exposed to a time-varying (sinusoidal) magnetic field will in turn emit acoustic and thermal energy due to the changes in size and viscous flexing of the material. An acoustic wave is defined as an elastic nonelectromagnetic wave with a frequency that may extend into the gigahertz (GHz) range. Acoustic transmission is that transfer of energy in the form of regular mechanical vibration through a gaseous, liquid, or solid medium. Acoustic emission is the phenomenon of transient elastic-wave generation due to a rapid release of strain energy caused by a structural alteration in a solid material (stress-wave emission). An ultrasonic wave is one that has a frequency above about 20 KHz Oust above human hearing). Additionally, exposure of a time-varying magnetic field will induce a time-varying current in a ferromagnetic sample such that it will emit electromagnetic (EM) energy.

As is known, electric and magnetic fields are fundamentally fields of force that originate from electric charges. Whether a force field may be termed electric, magnetic, or electromagnetic hinges on the motional state of the electric charges relative to the point at which field observations are made. Electric charges at rest relative to an observation point give rise to an electrostatic (time-independent) field there. The relative motion of the charges provides an additional force field called magnetic. That added field is magnetostatic if the charges are moving at constant velocities relative to the observation point. Accelerated motions, on the other hand, produce both time-varying electric and magnetic fields termed electromagnetic fields. See the textbook, *Engineering Electromagnetic Fields and Waves,* Carl T. A. Johnk, John Wiley & Sons, $2^{nd}$ Edition (1988). One well known wide use of these principles of electromagnetism is the transformer: An assembly having a ferromagnetic core around which a primary coil carrying a time-varying current is wound and a secondary coil is wound (into which an associated current is induced as a result of the time-varying magnetic field induced in the ferromagnetic core).

Anti-theft markers/tags (electronic article surveillance, EAS, markers) generally operate by "listening" for acoustic energy emitted in response to an interrogating ac magnetic field, to sense the presence of an EAS marker. Sensormatic, Inc. distributes an EAS tag (dimensions 3.8 cm×1.25 cm×0.04 mm) designed to operate at a fixed frequency of 58 kHz (well beyond the audible range of human hearing). These EAS tags are embedded/incorporated into articles for retail sale. Upon exiting a store, a customer walks through a pair of field coils emitting a 58 kHz magnetic field. If a tag is still in an article being carried by the customer, the tag will likewise emit a 58 kHz electromagnetic signal that can be detected using a pickup coil, which in turn may set off an audible or visual alarm. More-recently, these tags are being placed in a box-resonator, sized slightly larger than the tag, such as the tags placed within a cavity 20 of a housing (FIG. 2 of Winkler et al.).

The characteristic mechanical resonant frequencies $f_{mn}$ of a thin rectangular plate of given material, ends supported, are found using the following mathematical relationship (this is for out-of-plane vibrations only):

$$f_{mn} = \frac{Eh\pi}{24\rho(1-\sigma^2)}\left[\left(\frac{m}{a}\right)^2 + \left(\frac{n}{b}\right)^2\right] \quad [2]$$

where E is Young's Modulus of elasticity, σ is Poisson's ration, h is plate thickness, ρ is material density, and m and n are integers ≧1. Here, the closer the frequency of the interrogating time-varying magnetic field is to the fundamental acoustic resonant frequency, $f_{11}$, the greater will be the acoustic emission. As the frequency of the interrogating magnetic field moves away from the fundamental resonance frequency, $f_{11}$, the acoustic emission is reduced (thus, much harder to detect). Therefore, a thin rectangular plate more-efficiently absorbs energy and radiates at its fundamental acoustic resonant frequency. As suggested by the relationship [2], a rectangular thin film of given size and material (E and σ fixed) larger dimensions and greater material densities lead to lower resonant frequencies, with the response symmetrical about the resonant frequency.

As discussed above in connection with the definition of magnetostriction, an AC (time-varying) magnetic interrogating field applied to a magnetostrictive element causes the element to change shape at the frequency of the interrogation field. If the magnetic interrogation field is turned off, a magnetostrictive sensor element such as that shown at 26 or 56 in FIGS. 2A–B or FIG. 4 (which has been designed/built such that it is resonant at the interrogation frequency) will emit magneto-elastic energy which will convert, over a very short period of several hundred milliseconds, into electromagnetic (EM) energy that can be detected by suitably located EM detection coil(s). If the magnetostrictive element (for example, 26 or 56) is not resonate at the interrogation frequency, within a few microseconds the magneto-elastic energy being emitted from the element will be converted to heat.

For a ribbon or wire-shaped (or other such elongated shape, with a length greater than cross-sectional area, both ends free or supported) magenetostrictive element, first longitudinal resonant frequency is approximated by:

$$\omega_r = 2\pi f_r = \frac{\pi}{l}\sqrt{\frac{E(H \cdot T)}{\rho}} \quad [3]$$

where $f_r$ denotes the resonant frequency of the magnetoelastic element, l is the length of the element, E is Young's modulus of elasticity, and ρ is material density. Higher harmonic frequencies can be determined by multiplying the right-hand side of Equation 3 by successive integer values, i.e. n=1, 2, 3, 4, . . . Note that Young's modulus of a magnetostrictive piece of material is dependent upon temperature T and applied static magnetic field H. Thus, resonant frequency is proportional to temperature.

As will be discussed further in connection with FIGS. 4–7, rather than working at a fixed interrogation frequency and checking for ampitude like the anti-theft EAS markers do, the novel sensing apparatus and method of the invention looks to the frequency response of the sensor for sensing information about an analyte, temperature of the environment in which the sensor has been placed, viscosity or other property of a fluid, and pressure of a gas. The new sensing apparatus and method of the invention measure intensity of an acoustic, electromagnetic (EM), or other such emission: with the interrogation frequency at ($f_0-\Delta f$), and ($f_0+\Delta f$), where $f_0$ represents a value for the magneto-elastic resonant frequency (or a harmonic) of the sensor as built/sized; or, over a range of successive interrogation frequencies to identify the magneto-elastic resonant frequency or harmonic thereof (generally, sensor resonance will correspond with a relative maximum of the emission intensity values). In effect, the interrogation field acts as a power source for the sensing apparatus of the invention with a sensor structure operating as passive elements with no mechanical linkages/connections subject to wear. Thus, a sensor structure's product life is generally limited by physical properties (e.g., strength/durability) of the materials used, the responsiveness of the outer layer(s), and the type of environment within which the sensor operates (e.g., whether caustic or under extreme temperature functions, and whether additional static or fluid dynamic forces will act on the sensor, and so on).

One suitable base magnetostrictive material is the amorphous cobalt based alloy known as METGLAS® 2826 MB, that has been vacuum annealed in the presence of a DC magnetic field to enhance magnetostriction, commercially distributed by Allied Signal, Inc. in New Jersey; another available magnetostrictive amorphous Co-based magnetically soft alloy is ATALANTE® film, commercially distributed by Innovative Sputtering Technology N.V. of Karreweg, Belgium (which is widely used throughout Europe as an anti-theft retail item marker). The composition, and any tempering done, of the material chosen for the magnetostrictive base element will affect operating characteristics of a sensor structure built therewith. If sensing an analyte, it is preferable to choose a base magnetostrictive material that remains relatively stable (i.e., its material properties do not change a significant amount) over a wide range of operating temperatures. If sensing temperature of an environment with a sensor structure that has no thermally responsive layer, it is preferable to choose a base material capable of significant change with fluctuations in temperature to change its emission frequency.

Turning, now, to FIG. 4 which illustrates preferred analyte and temperature sensing apparatuses of the invention in schematic-block diagram form, one can see that sensor structures similar to those depicted in FIGS. 1A, 2A, and 3 have been positioned within an environment defined by boundary 50. Boundary 50 represents a multitude of different environments of varying sizes and conditions within which the analyte in question (or a property thereof), the viscosity of a fluid contained within, and/or the temperature is sensed. By way of example, the sensor environment might be one encountered in a biomedical application (such as in vivo or in vitro, within or in proximity to a medical test sample, and so on). Or, the environment might be one encountered when: performing food quality/inspection (such as sealed packaging within which, or in proximity to, moisture or airborne germ(s) are monitored); monitoring of heavy metals found in groundwater, treated water, or wastewater (flowing in natural or manmade waterways, canals, wells, or pipes), and monitoring waste from manufacturing processes (whether the waste takes the form of solid, aqueous solution, or gas pollutants).

For illustrative purposes, the several sensors (labeled 51, 30, 20', 55) shown within boundary 50 at various orientations for independent movement throughout boundary 50, are sized quite large relative to the overall size of the environment. In many applications, only one such sensor is needed within an environment being sensed. However, where a "package" of sensing information is desired, several separate sensor structures freely "floating about", or an ordered array of sensor structures fabricated along (extending from, embedded within or atop a support member such as those shown at 150, 170, 190, 210 in respective FIGS. 10A–B, 11A–B, and 12) with an overall length "l"

(labeled in FIG. 12) on the order of several centimeters to micrometers and smaller, may be positioned within an environment. As one can see, a considerable range of sizes is available. An apparatus capable of providing a package of sensing information is used, for example, where one needs to know viscosity of a solution/analyte (or some other fluid) contained within the environment, the chemical composition of an analyte, presence or absence of a pollutant within the environment, temperature fluctuations of the environment on a real-time basis, historical temperature information, and humidity or moisture content. Each sensor structure of such an array is preferably designed and built (sized/shaped and materials) to operate over a slightly different frequency range than the other sensors within the array. This makes it easier to distinguish emissions received (or, "listen for" an emission) from each particular sensor of the array. In this case, the receiving unit would sweep over a larger range of frequencies that includes at least each of the frequency sub-ranges of the individual elements. Sensors within an environment are preferably sized relative to the overall volume of the environment. By way of example: A sensor used in vivo (within a living cell or organism) or within food packaging may need to be built on a micro-circuit scale, whereas a sensor positioned outside a smokestack or within a sealed pipe can be built on a much larger scale to facilitate ease of monitoring. Furthermore, sensor size is dependent upon sensitivity of the receiver used to measure energy emission from the sensor. For example, a sensor from which EM emission is detected to determine temperature of an environment might be sized on the order of $20 \times 10^{-6}$ in$^3$ whereas a temperature sensor from which acoustic emission intensity is detected with an acoustic receiver capable of making less-sensitive readings, would be sized approximately 15 times larger (or, $300 \times 10^{-6}$ in$^3$).

It may be desirable (and, in some cases necessary) to cap the chemically, frictionally, or thermally responsive layer (such as 52 adhered to base 53 of sensor 51 and those labeled 27, 28 which sandwich magnetostrictive base 26 of sensor 20') with a protective or bio-compatible coating, such as titanium, especially in the event the sensor is placed within an environment (50) that is chemically harsh or within a human body (such as the stomach). It is preferred that the chemically responsive layer not be completely sealed by such a coating so as not to degrade its responsiveness to the analyte, or property thereof, or temperature. Also illustrated in FIG. 4 are magnetizable ON-OFF switches made of a magnetically hard material (see discussion of the MHM layer 19 shown, for example, adhered to base 16 in FIG. 1B): ON-OFF switch element 54 is a stand alone located in proximity to sensor 51; and switch element 57 is shown adhered to magnetostrictive base element 56. A MHM element 19, 16 may also double to generate a DC bias field superimposed over the time-varying field applied, to create a dedicated designer-field surrounding a particular sensor. Suitable magnetically hard materials for switch elements include ferromagnetic metal alloys and their oxides, made to support large external fields.

The preferred analyte and temperature sensing apparatus of the invention depicted in block form at 40 in FIG. 4 includes a transmitting subassembly having a frequency generator or oscillator 42 whose output is fed to a power amplifier 44 which, in turn, feeds a time-varying field generating coil 46. A receiving subassembly is depicted at 60. The field generating coil 46 establishes an alternating magnetic field of desired frequency and amplitude in the environment bounded by dashed line 50. The amplitude of the field necessary to generate a predetermined signal level (sensor amplitude response) will vary depending upon system parameters such as coil size, sensor magnetoelastic properties, and sensitivity of receiving electronics. Operating characteristics of the sensor can be controlled by superimposing a DC bias magnetic field upon the AC magnetic field generated by coil 46. It may be desirable, and even necessary, to create a dedicated designer-field, if you will, consisting of DC and AC magnetic field components, around a sensor in operation to maximize the emission response thereof (making it more-predicable) depending upon design (size/shape and materials used) of the sensor. The resonant frequency value for a sensor of given size/shape and material can be identified by measuring successive values for emission intensity taken over an operating range of interrogation frequencies. In the event a DC bias field is superimposed within boundary 50, the identification of the sensor's resonant frequency could be done by either holding the frequency of the DC bias field fixed and varying (sweeping over) the frequency of the AC field, or holding the AC field fixed and varying the DC bias field strength.

A DC bias field superimposed as explained above, may be generated by simply passing a DC current through a coil positioned an appropriate distance from the sensor, or this DC bias field may be generated by other suitable means. One useful way to provide a DC bias field around a sensor structure is to position a magnetized (activated) appropriately-sized magnetically hard material (MHM) element nearby, such as that shown in FIG. 4 at 54 (explained above in connection with use as an ON-OFF switch for the sensor). The use of an activated MHM element is preferred in the event it becomes necessary to superimpose dedicated bias fields (thus, creating a dedicated designer-field) surrounding each sensor structure of an array of sensors within one environment. This is especially useful if a selected "package" of sensing information is sought from one single environment, and at least two (or all) of the sensor structures needed to provide that selected package of sensing information operates/resonates more-effectively when immersed within different dedicated designer-fields.

A receiving unit 62 is needed for measuring magnetoelastic emissions emanating from the sensor. Suitable emission detection circuitry (represented by box 62b in FIG. 4) is in communication with a field/emission receiving coil. The specific type of receiving coil 62a used to detect emissions 58 from any one, or several, of the sensors within boundary 50 will depend upon the type of emission being received. For example, a sensor built for efficient emission of acoustic (elastic) waves according to relationship [1] will be paired with a suitable electroacoustic transducer; likewise, a sensing apparatus designed for detecting electromagnetic emission must be paired with a suitable EM pick-up coil. Electroacoustic transducers that operate over a range of frequencies from 1 kHz to 100 kHz to measure acoustic emissions are available, such as those distributed by APO Acoustics of Belmont, Calif. EM pick-up coils suitable for use, here, that operate up to 1 MHz are readily available. If receiving EM emissions, prior to measuring the intensity thereof, one can turn off the time-varying magnetic field and "listen" for an EM response that takes place (over a very short period of time, on the order of hundreds of milliseconds) due to the conversion of the magneto-elastic energy to EM energy at the resonating frequency of the sensor. Note however, that it is not necessary to turn of the time-varying magnetic field to receive EM emissions.

Information gathered about the environment by the receiving unit 62 is sent to a processing unit 64 (such as a dedicated microprocessor controlled by software components or subroutines to perform data processing and manipulation for an apparatus or method of the invention) which is, in turn, connected to a user interface 68 of suitable type such as a monitor screen (whether or not touch-sensitive) displaying alphanumeric or waveform information, one or more light emitting diode (LED) indicators (such as a display of color-coded LEDs), automatic audio message or siren, and so on. Depending upon the nature and location of the environment being sensed, the user interface may necessarily be located nearby, or several hundreds of miles from the environment (depicted within boundary 50) and processing unit 64 to communicate via digital phone line, coaxial cable, or satellite link.

Figure 6:
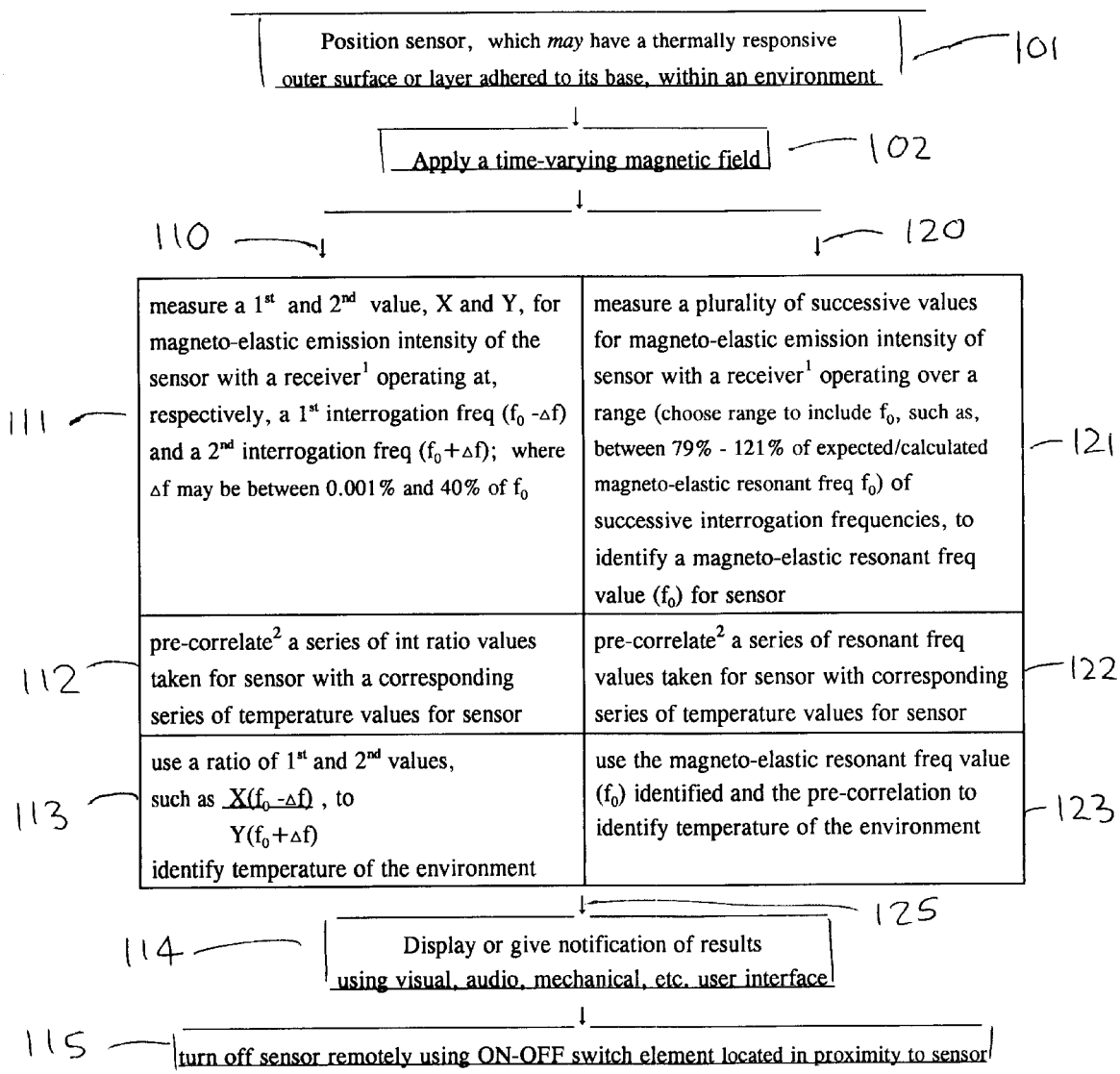
FIG. 6 is a flow diagram detailing alternate preferred steps of a method of sensing a temperature of an environment as further described herein.
Figure 7:
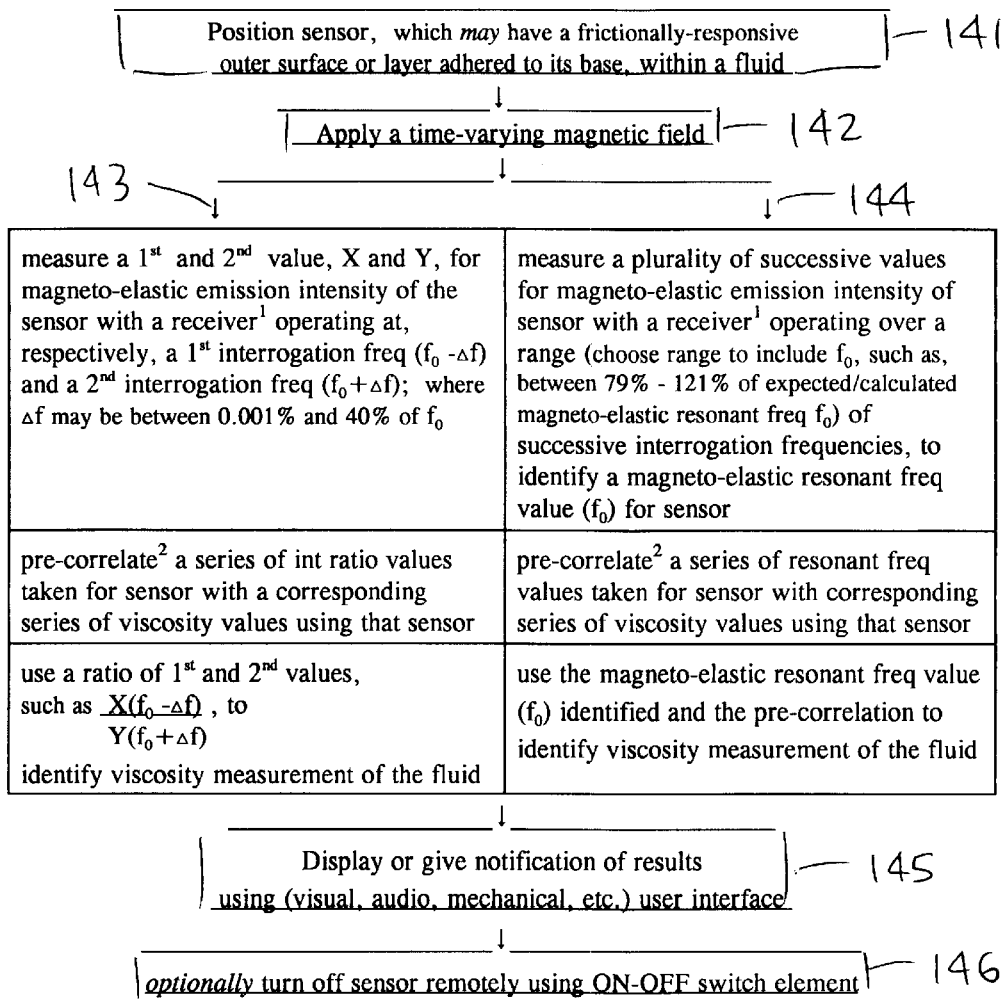
FIG. 7 is a flow diagram detailing alternate preferred steps of a method of sensing a fluid viscosity as further described herein.
Figure 16:
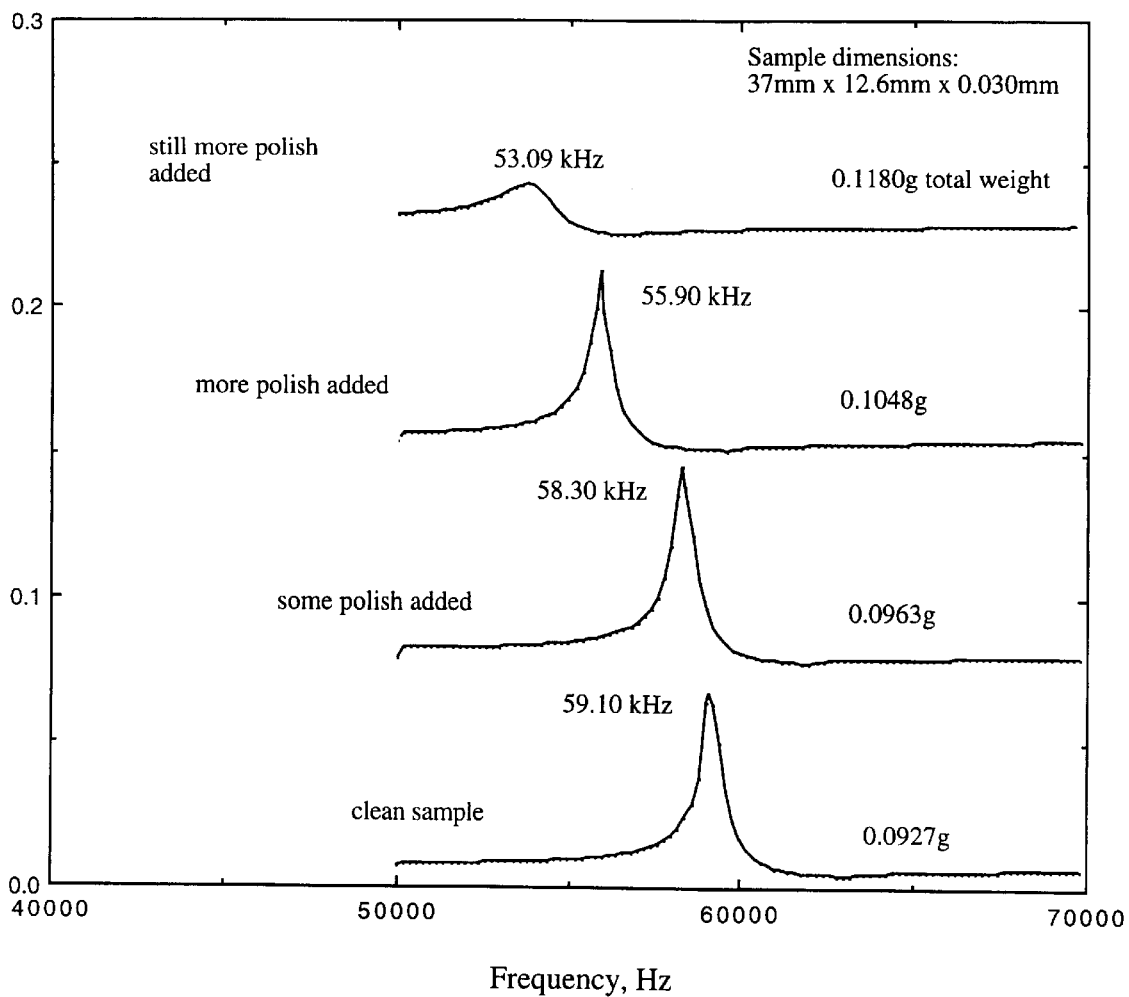
FIG. 16 is a graphical representation 240 illustrating how resonant frequency shifts (resonant frequency for each graph is found at relative maximum(s) where voltage spikes occur due to efficient magneto-elastic emission from the sensor), for a sensor structure of the invention as mass changes (as shown here, mass increases).

Operation of, and flexibility in design of, the preferred sensing apparatus (to include features from that shown in block form at 40 in FIG. 4) of the invention can be appreciated better in connection with the preferred, novel method of sensing an analyte (70 in FIG. 5) and associated novel methods of sensing temperature of an environment (100 in FIG. 6) and sensing viscosity (140 in FIG. 7). As mentioned earlier, the sensing apparatus and method measure intensity of the magneto-elastic (acoustic and EM) emission from a remotely-located sensor using a novel approach: (A) with the time-varying interrogation frequency at $(f_0-\Delta f)$, and $(f_0+\Delta f)$, where $f_0$ represents a value for the magneto-elastic resonant frequency (or harmonic thereof) of the sensor as built/sized and $\Delta f$ is likely a value between 0.001% and 40% (and more-preferably under 20%) times the resonant frequency $f_0$; and/or (B) over a range of successive interrogation frequencies, preferably including at least the resonant frequency (or a harmonic thereof) of the sensor, to identify the magneto-elastic resonant frequency (or harmonic, as the case may be). By and large, the sensor's resonant frequency and its harmonics correspond with a relative maximum of the emission intensity values (where emissions are maximized). This can be see by the graphical representation in FIG. 16 made by taking measurements from a sensor with base element 37 mm×12.6 mm×0.03 mm in size made out of a METGLAS® amorphous metallic glass (here an FeCoBNb alloy was used and vacuum annealed in the presence of a magnetic field of 1000 oersted).

In the case of approach (A) above, of greatest interest is a ratio of emission intensity values taken on either side of the resonant frequency $f_0$, i.e., $X(f_0-\Delta f)/Y(f_0+\Delta f)$, which can be pre-correlated with a corresponding series of mass change values (see the graph in FIG. 8), viscosity values, or temperature values to sense the analyte (its property), viscosity, or temperature. In the case of approach (B) above, pre-correlations can be readily made for the sensor of a series of resonant frequency values with corresponding mass change values (FIG. 15), with material stiffness values, with fluid viscosity values (FIG. 9) or with corresponding temperature values. Such a pre-correlation can then be used in identifying an analyte composition and/or concentration, pH measurement, fluid viscosity, temperature of the environment, as the case may be. By way of example only, a series of interrogation frequencies taken in 10 kHz intervals to measure a corresponding series of emissions from a sensor 1 cm×2 cm×20 microns thick sensed a 0.5 mg mass change at 60 kHz.

Figure 5:
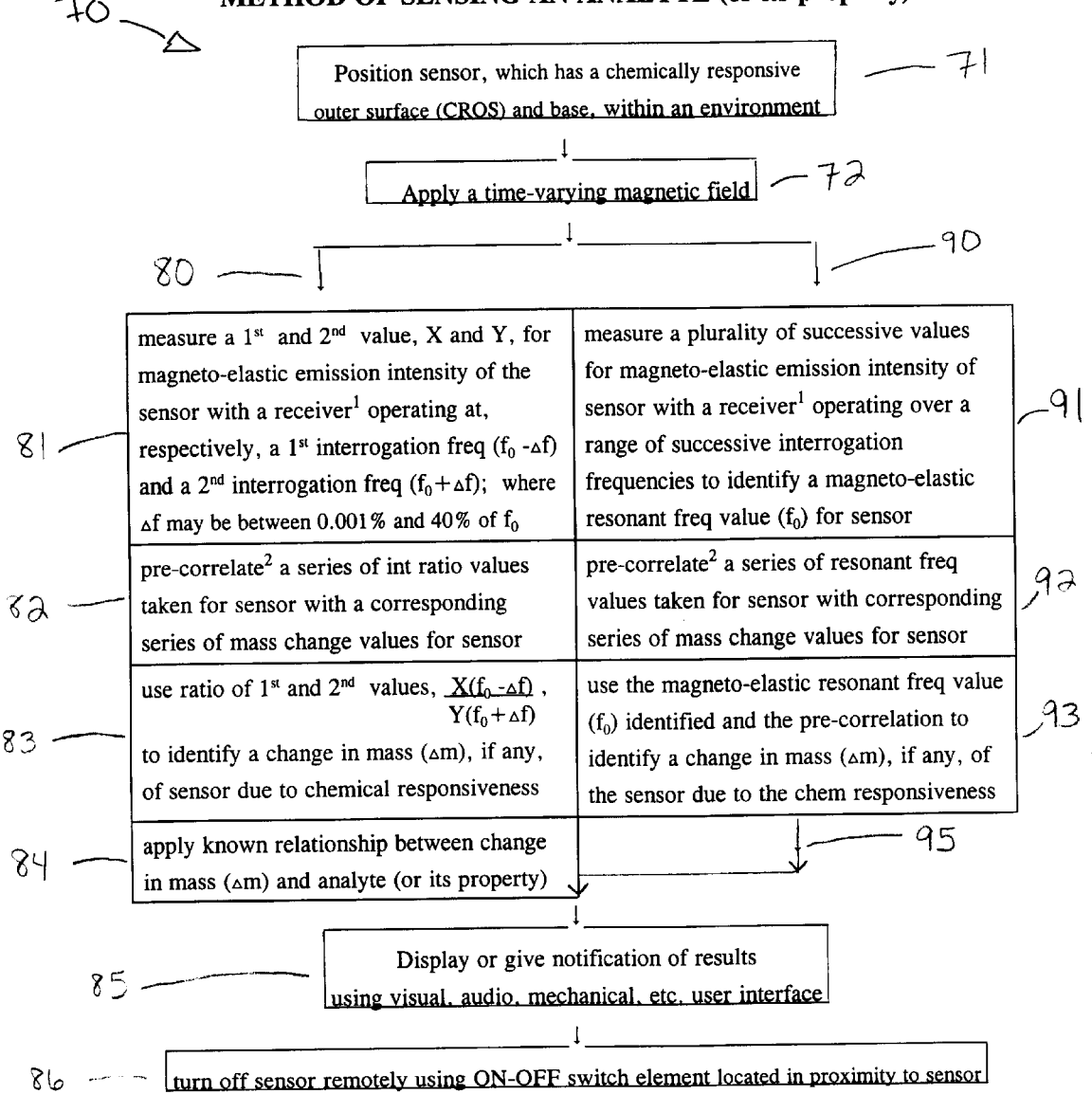
FIG. 5 is a flow diagram detailing alternate preferred steps of a method of sensing an analyte as further described herein.

FIG. 5 is a flow diagram of a preferred method of sensing an analyte (or property thereof) at 70. First the sensor, which has a chemically responsive outer surface adhered to a base, is positioned within an environment (such as the one bounded by dashed line 50, FIG. 4). Next, a time-varying interrogation magnetic field is applied (for example, by transmitting subassembly described in connection with FIG. 4). Footnotes (at 87) included at the bottom of FIG. 5 point out that one may choose to turn-off the time-varying interrogation field just prior to taking emission intensity measurements, in the event doing so leads to a more-accurate or stronger emission measurement. As mentioned, it may be desired (and perhaps necessary) by this point in the process, to activate a MHM element to generate a DC bias field that is superimposed on the time-varying field to produce a dedicated designer-field surrounding the sensor. Thereafter, two paths are shown: one labeled by arrow 80 and one labeled by arrow 90. Under 80, as described in box 81, a first and second value for magneto-elastic emission intensity, X and Y, are measured with a receiving unit (62 in FIG. 4) operating at, respectively, a first interrogation frequency such as $(f_0-\Delta f)$ and a second interrogation frequency such as $(f_0+\Delta f)$. As mentioned above, $\Delta f$ is preferably a value between 0.001% and 40% (more-preferably 20%) of $f_0$ (a value not too far from $f_0$) with $f_0$ representing either the resonant frequency or a harmonic thereof.

Figure 8:
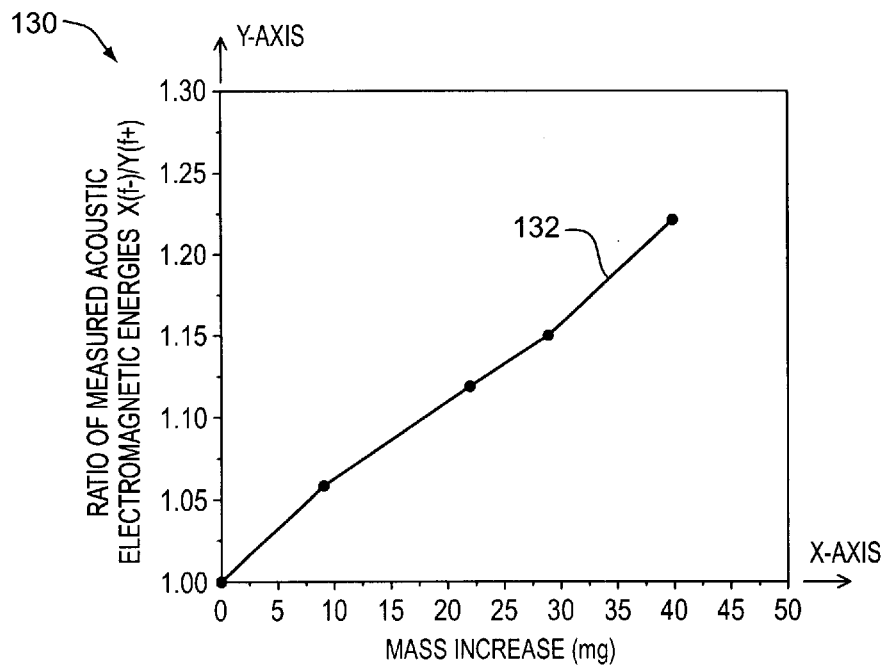
FIG. 8 is a graphical representation 130 of a correlation 132 between a series of emission intensity ratio values labeled $X(f_0-\Delta f)/Y(f_0+\Delta f)$ along the vertical Y-axis, taken for a preferred analyte sensor and a corresponding series of mass change values along the horizontal X-axis, taken for that sensor: $f_0$ represents resonant frequency (or a harmonic thereof) of the sensor, $X(f_0-\Delta f)$ represents a value for emission intensity taken at a first interrogation frequency $(f_0-\Delta f)$, and $Y(f_0+\Delta f)$ represents a value for emission intensity taken at a second interrogation frequency $(f_0+\Delta f)$.

Turn, now, for a moment to the graphical representation 130 in FIG. 8. This is an example of the type of pre-correlation suitable for use to identify mass change in the next step (box 83). The FIG. 8 graph represents a series of emission intensity ratio values (y-axis) experimentally taken for a sensor of given size and material(s) with corresponding mass change values (x-axis) for that sensor (for reference, see box labeled 82 of FIG. 5). When in operation, as indicated by box 83 (FIG. 5), once emission intensity values are taken for a sensor of the same size and material(s) and a ratio, $X(f_0-\Delta f)/Y(f_0+\Delta f)$, is computed using a suitable processing means, one can identify a change in mass ($\Delta m$), if any, of the sensor due to chemical responsiveness of the layer. Likewise, if no $\Delta m$ is detectable and instead the chemical responsiveness causes a change in material stiffness of the sensor, one could use a pre-correlation made between material stiffness and resonant frequency for a sensor structure. Applying a prior experimentally-determined relationship between change in mass ($\Delta m$), or material stiffness, of that sensor (as sized with same materials) and the presence and/or amount of chemical analyte (see box 84), one can obtain specific information about an analyte, such as presence and/or concentration, or a property thereof. The sensing information results obtained therefrom can be communicated to the user interface (box 85). As represented in the box labeled 86, once finished with a series of measurements taken from a particular sensor, a remote ON-OFF switch (as described above in connection with FIG. 4) can be optionally activated to turn-off the sensor. It might be desirable, or even necessary, to turn off a first sensor so that a second or third sensor of an array can be "heard" without interference from any accidental resonation of the first sensor.

Figure 15:
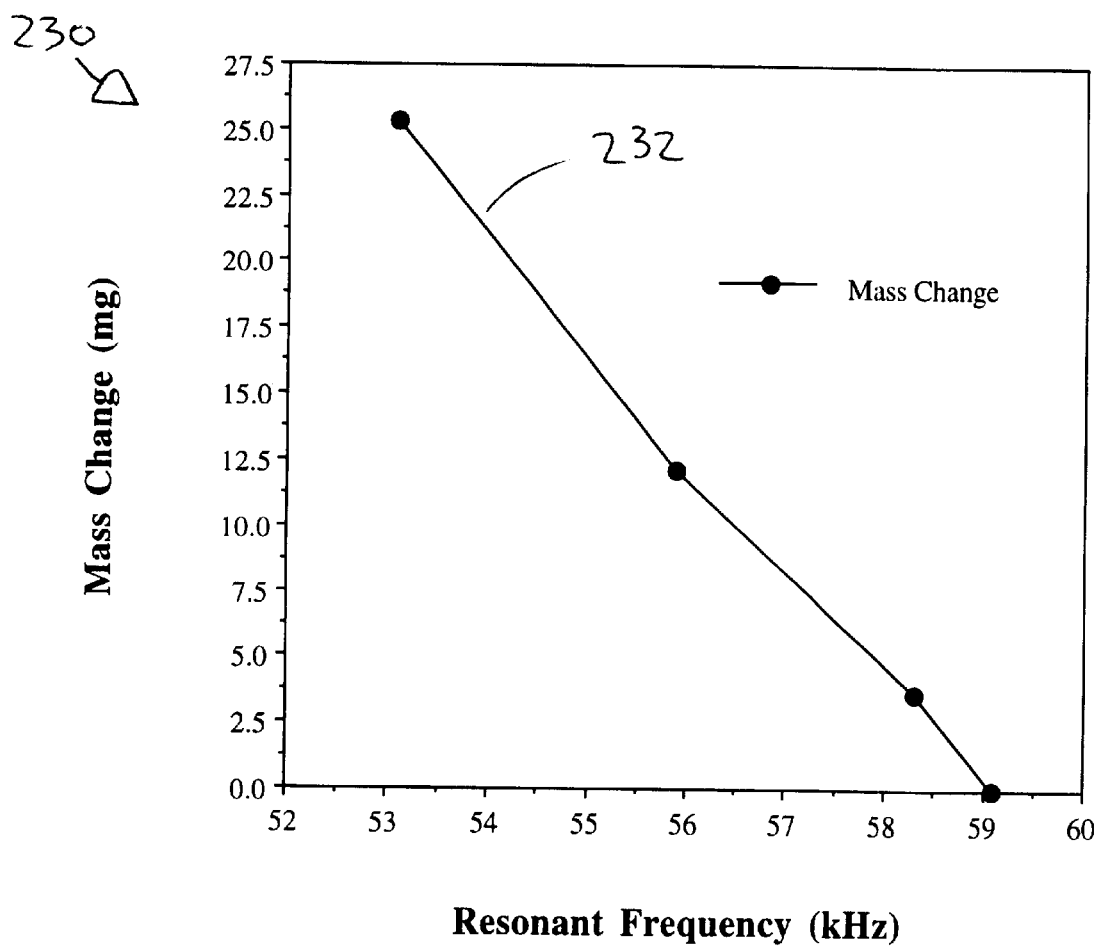
FIG. 15 is a graphical representation 230 of a correlation 232 between a series of resonant frequency values along the x-axis, taken for an analyte sensor and a series of mass change values for that sensor.

Following, instead, the arrow illustrated in FIG. 5 at 90, one can measure a plurality of successive values for emission intensity of a sensor structure with a receiving unit (62) operating over a range of successive interrogation frequencies to identify a resonant frequency value, $f_0$, for the sensor (box 91). A pre-correlation (experimentally-determined) of a series of resonant frequency values taken for a particular sensor with corresponding series of mass change ($\Delta m$) values for that sensor (box 92) would be done prior to the step identified at 93. Then, the resonant frequency value (or a harmonic thereof), $f_0$, identified in step 91 and the pre-correlation relationship determined from step 92 are used to identify any change in mass of the sensor in operation, due to chemical responsiveness. A sample graphical representation of a pre-correlation (92) is shown in FIG. 15 at 232:

Here a base element 20 microns×3.8 cm×1.8 cm in size, made out of a METGLAS® amorphous metallic glass (FeCoBNB alloy vacuum annealed) was used. As mentioned in connection with the process following arrow 80, the sensing information results obtained from step 93 can, likewise, be communicated (arrow 95) through a user interface (box 85).

If more information about an environment is desired, additional steps to the method 70 in FIG. 5 include: measuring a second plurality of successive values for magneto-elastic emission intensity of a second sensor with a receiver (such as depicted in FIG. 4 at 62) operating over a second range of successive interrogation frequencies to identify a magneto-elastic resonant frequency value for the second sensor, and pre-correlating a second series of resonant frequency values taken for the second sensor and a corresponding second series of mass change values for this second sensor; and/or measuring a third and fourth value for magneto-elastic emission intensity of a second sensor with the receiver operating at, respectively, a third and fourth interrogation frequency. The same, or an additional, receiver may be used to measure emission from the second sensor. In order to provide a package of valuable sensing information, several sensor structures can be incorporated in an ordered array (as explained in connection with FIGS. 10A–B, 11A–B, and 12), or each could be built as separate sensing structures for free independent movement throughout the environment.

FIG. 6 is a flow diagram of a preferred method 100 of sensing temperature of an environment. First the sensor, which may have a thermally responsive outer surface adhered to a base, is positioned within an environment (such as the one bounded by dashed line 50, FIG. 4). Next, a time-varying interrogation magnetic field is applied (for example, by transmitting subassembly described in connection with FIG. 4). Footnotes (at 117) included at the bottom of FIG. 6 point out that one may choose to turn-off the time-varying interrogation field just prior to taking emission intensity measurements, in the event doing so leads to a more-accurate or stronger emission measurement. As mentioned, it may be desired (and perhaps necessary) by this point in the process, to activate a MHM element to generate a DC bias field that is superimposed on the time-varying field to produce a dedicated designer-field surrounding the sensor.

As in FIG. 5, two paths are shown in FIG. 6: one labeled by arrow 110 and one labeled by arrow 120. Under 110, as described in box 111, a first and second value for magneto-elastic emission intensity, X and Y, are measured with a receiving unit (such as 62 in FIG. 4) operating at, respectively, a first interrogation frequency such as ($f_0-\Delta f$) and a second interrogation frequency such as ($f_0+\Delta f$): $\Delta f$ being preferably a value between 0.001% and 40% of $f_0$ (more-preferably 20%, a value closer to $f_0$). Next, at 112, a pre-correlation is made between a series of emission intensity ratio values taken for the sensor and a corresponding series of temperature values for that sensor (similar to that graphically represented at 130 in FIG. 8). Then, a ratio such as X($f_0-\Delta f$)/Y($f_0+\Delta f$) is computed using a suitable processing means to identify temperature. A display or other notification of results can be done (following arrow 125 to box 114). And, as explained above in connection with box 86, the sensor can optionally be remotely turned off.

Following, instead, the arrow illustrated in FIG. 6 at 120, one can measure a plurality of successive values for emission intensity of a sensor structure with a receiving unit (e.g., 62, FIG. 4) operating over a range of successive interrogation frequencies to identify a resonant frequency (or harmonic) value, $f_0$, for the sensor (box 121). A pre-correlation (experimentally-determined) of a series of resonant frequency values taken for a particular sensor with corresponding series of temperature values for that sensor (box 122) may be done prior to the step identified at 123. Then, the resonant frequency value, $f_0$, identified in step 121 and the pre-correlation relationship determined from step 122 can be used to identify temperature. One could graphically represent the pre-correlation (122) in a form similar to the FIG. 15 representation 230. As mentioned in connection with the process following arrow 110, the sensing information results obtained from step 123 can, likewise, be communicated (labeled arrow 125) through a user interface (box 114). Again, optionally the sensor can be remotely turned off (115).

If more information about an environment is desired, additional steps to the method 100 in FIG. 6 include: measuring a second plurality of successive values for magneto-elastic emission intensity of a second sensor with a receiver (such as depicted in FIG. 4 at 62) operating over a second range of successive interrogation frequencies to identify a magneto-elastic resonant frequency value for the second sensor, and pre-correlating a second series of resonant frequency values taken for the second sensor and a corresponding second series of mass change values for this second sensor; and/or measuring a third and fourth value for magneto-elastic emission intensity of a second sensor with the receiver operating at, respectively, a third and fourth interrogation frequency. As mentioned, the same or an additional receiving device may be employed to measure emission from the second sensor.

The operation of a novel viscosity sensor and associated method of the invention is based upon monitoring the frequency shift of magnetoelastic resonance of a magnetostrictive strip of amorphous metallic glass. Forces of friction act on liquid immediately surrounding the sensor due to the vibrational motion of the sensor when placed within a time-varying magnetic field. For purposes of the discussion, below, the vibrating magnetoelastic sensing structure is considered to be constrained between two rigid plates. Certain restrictions have been placed on the solutions to simplify this discussion.

Mathematically, the influence of the viscosity and density of a fluid, such as liquid, on the longitudinal vibratory motion of the strip is reflected by the addition of a friction force term in the equation of motion of the strip-shaped sensor given below:

$$(\partial^2 u/\partial t^2) = E/[\rho(1-\sigma^2)](\partial^2 u/\partial y^2) - [2\eta k u \cot(kh)/\rho. \tag{4}$$

for a strip in the yz-plane (long axis of sample along the y direction, short direction along the z, and thickness in the x, ac field applied along y direction) of a rectangular coordinate system vibrating along the y-axis. In the above equation, u denotes the displacement vector of the wave; E, $\rho$, $\sigma$ are the Young's modulus, density and Poisson ratio of the strip material; h is the thickness of the fluid film on both sides of the strip (i.e. the distance between the vibrating and the steady plate); $\eta$ is the viscosity of the fluid, k is the (complex) wave vector of the transversal wave set up by the vibrating strip and propagating in the liquid in an orthogonal direction to the plane of the strip and is given by the following expression:

$$k = (1+i)/\delta \tag{5}$$

where i denotes the square root of minus one in complex notation. $\delta = \sqrt{[(2\eta/(\rho_1\omega)]}$ is the depth of penetration, a measure of the wave amplitude damping ($\rho_1$-fluid density), $\omega$ is the radian frequency, $2\pi f$.

The metallic glass viscosity sensor will exhibit magnetostrictive vibrations at almost any frequency of the driving AC magnetic field. These vibrations, however, are most pronounced at specific frequencies, corresponding to those of its mechanical resonance (determined by both material and size). The sensor's response will be monitored at one of these frequencies (mostly at its fundamental frequency, but also at harmonics), an appropriate dispersion relation is expressed below:

$$\omega_n^2 = \{E/[(\rho(1-\sigma^2)](n\pi/l)^2\} - \{[2\eta/(\rho\delta)]\cdot[(\sin h(2h/\delta)+\sin(2h/\delta)]/[(\cos h(2h/\delta)-\cos(2h/\delta)]\} \quad [6]$$

The first term on the right-hand-side of this equation represents the nth harmonic of the resonant frequency of the sensor in an inviscid fluid (air is a good approximation); the second term reflects the influence of the shear forces (or forces of friction) on both outer surfaces of the sensor. Replacing certain terms on the right-hand-side of equation [6] one obtains the following expression for the resonant frequency shift, where $\omega_0$ is the resonant frequency in inviscid fluid:

$$2\omega_0\Delta\omega - (\Delta\omega)^2 = \{[2\eta/(\rho\delta)][\sin h(2h/\delta)+\sin(2h/\delta)]/[(\cos h(2h/\delta)-\cos(2h/\delta)] \quad [7]$$

Consider the two limiting cases of highly viscous and inviscid fluids:

a) For a highly viscous fluid ($h/\delta \ll 1$), $\Delta\omega = (\rho h\omega_0)^{-1}\eta$ i.e. the frequency shift is proportional to the dynamic viscosity of the fluid.

b) For an almost inviscid fluid ($h/\delta \gg 1$) $\Delta\omega = [\eta\rho_1/(2\rho^2\omega_0)]^{1/2}$ i.e. $\eta\rho_1 \sim (\Delta\omega)^2$ and in order to separate the contribution of the viscosity, a prior knowledge of the density of the fluid is necessary.

FIG. 7 is a flow diagram of a preferred method 140 of sensing viscosity of a fluid within an environment. Every fluid has certain characteristics by which its physical condition may be described. Viscosity, mass density, and specific heat are a few of the many properties used to describe the physical condition of a fluid. By way of example, we focus our discussion, here, on viscosity. Viscosity is a function of temperature, pressure, and density of a fluid, and are thus interrelated by known relationships. First the sensor, which, as noted in FIG. 7 may have a frictionally responsive outer surface adhered to a base, is positioned (or immersed) within an environment containing a fluid. Next, a time-varying interrogation field is applied 142 (for example, by transmitting subassembly described in connection with FIG. 4). Footnotes (at 147) included at the bottom of FIG. 7 point out that the receiver type will depend upon the type of emission being received. As mentioned, it may be desired (and perhaps necessary) by this point in the process, to activate a MHM element to generate a DC bias field that is superimposed on the time-varying field to produce a dedicated designer-field surrounding the sensor.

As in FIGS. 5 and 6, two paths are shown in FIG. 7: one labeled by arrow 143 and one labeled by arrow 144. Under 143, a first and second value for magneto-elastic emission intensity, X and Y, are measured with a receiving unit (such as 62 in FIG. 4) operating at, respectively, a first interrogation frequency such as $(f_0 - \Delta f)$ and a second interrogation frequency such as $(f_0 + \Delta f)$: $\Delta f$ being preferably a value between 0.001% and 40% (more-preferably 20%) of $f_0$. Next, a pre-correlation is made between a series of emission intensity ratio values taken for the sensor and a corresponding series of viscosity values for that sensor (similar to that graphically represented at 130 in FIG. 8). Then, a ratio such as $X(f_0-\Delta f)/Y(f_0+\Delta f)$ is computed using a suitable processing means to identify viscosity. A display or other notification of results can be done 145. And, as explained above, the sensor can optionally be remotely turned off 146.

Figure 9:
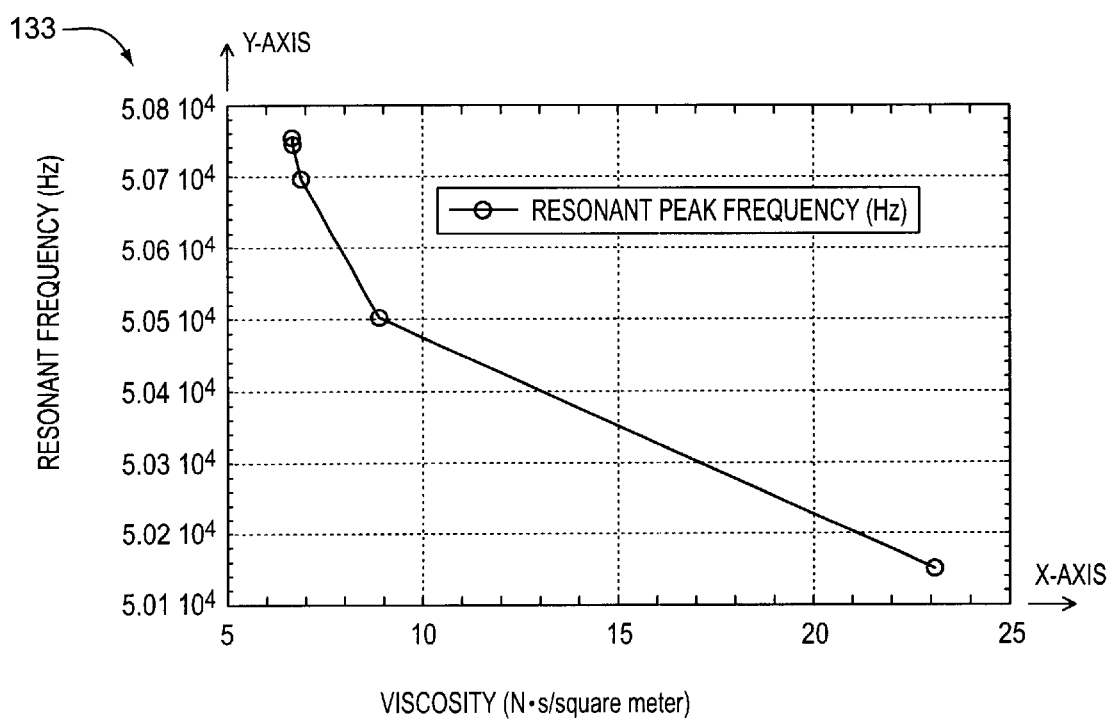
FIG. 9 is a graphical representation 133 of a correlation 134 between a series of resonant frequency values along the y-axis, taken for a preferred viscosity sensor and a series of viscosity values for that sensor.

Following, instead, the arrow illustrated in FIG. 7 at 144, one can measure a plurality of successive values for emission intensity of a sensor structure with a receiving unit (e.g., 62, FIG. 4) operating over a range of successive interrogation frequencies to identify a resonant frequency (or harmonic) value, $f_0$, for the sensor. A pre-correlation (experimentally-determined) of a series of resonant frequency values taken for a particular sensor with corresponding series of viscosity values for that sensor would be done. Then, the resonant frequency (or harmonic) value, $f_0$, identified and the pre-correlation relationship determined can be used to identify viscosity. A sample graphical representation of a pre-correlation is shown in FIG. 9 at 134: Here a base element 20 microns×3.8 cm×1.8 cm in size, made out of a METGLAS® amorphous metallic glass (FeCoBNb alloy vacuum annealed) was used. As mentioned in connection with the process following arrow 143, the sensing information results obtained can, likewise, be communicated through a user interface by, for example, displaying the sensing results obtained on a screen (box 145). Again, optionally the sensor can be remotely turned off 146.

Figure 10A:
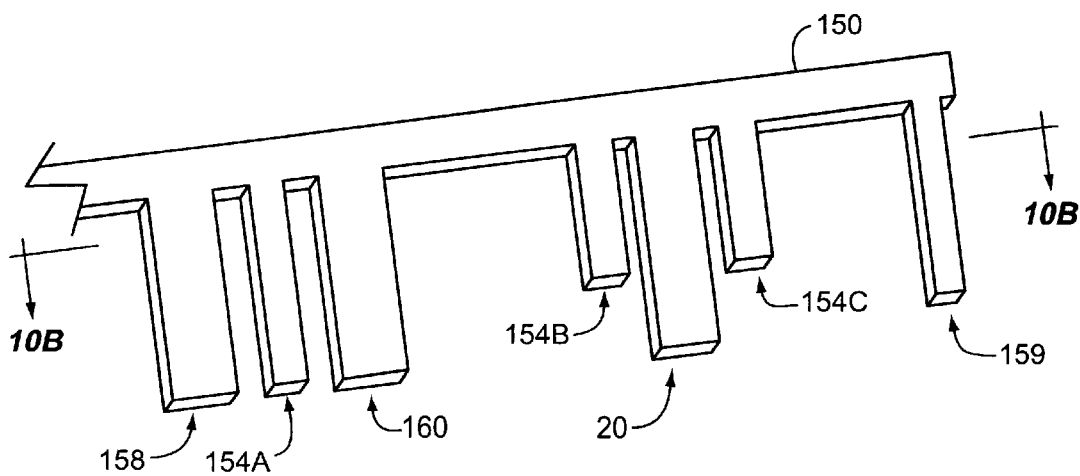
FIG. 10A is an isometric view of an alternate sensing apparatus having several sensor structures ordered in an array extending from a support member 150 as could be used if a "package" of sensing information is desired from one environment.
Figure 10B:
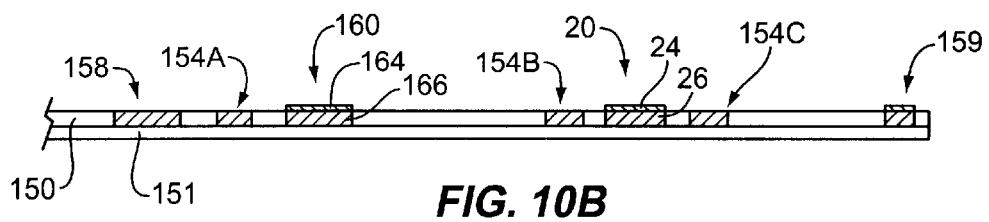
FIG. 10B is a sectional view taken along 10B—10B of FIG. 10A showing the array.

As mentioned, several sensors may be needed to provide a package of different types of sensing information, as mentioned above. Each such sensor may have a dedicated designer-field produced by superimposing a DC bias field generated by a MHM element (such as those shown at 154a, 154b, 154c, 54 in FIGS. 10A–B, 11A–B, 12) onto the time-varying field within which the sensor is positioned. The array shown in FIGS. 10A–B, 11A–B, 12 illustrate ways to implement this. Turning first to FIGS. 10A–B, several elongated sensors 158, 160, 20, and 159 are shown extending from a support member 150. To illustrate the flexibility of this sensing apparatus design, a couple of these sensors, 160 and 20 (also illustrated in FIGS. 2A–B) have responsive outer layers 164, 24 respectively, whereas sensor structures 158 and 159 do not. Layers 164, 24 may have chemically, frictionally, or thermally responsive outer surfaces. The whole array may be supported by an additional layer of a flexible material such as Kapton Polyimide film made by DuPont, shown only in FIG. 10B at 151. It is important that this material be flexible to allow vibration of the sensing structures.

Figure 11A:
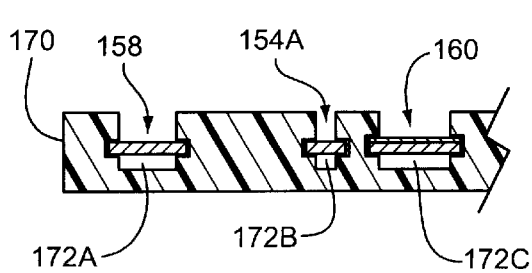
FIG. 11A is a partial sectional view of an alternate means for securing sensor structures (such as those labeled 158 and 160) in sliding fashion, to a support structure 170.

FIG. 11A illustrates a support member 170 having several chambers 172a–c slidably retaining sensor structures 158 and 160 (also shown in FIGS. 10A–B), as well as a MHM element 154a to generate a superimposed DC bias field or operate as an ON-OFF switch.

Figure 11B:
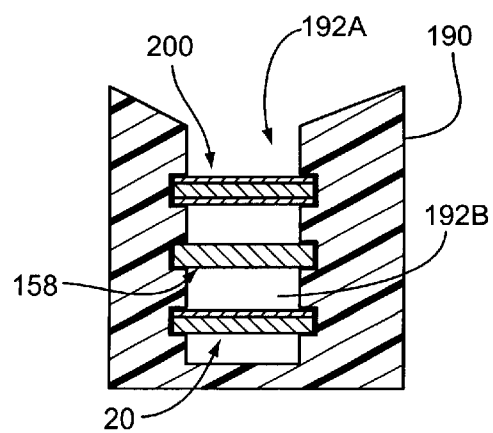
FIG. 11B is a sectional view of another alternate means for securing sensor structures positioned such as the elements labeled 20, 158, and 200 are shown in stacked relationship within a chamber 192b (open at its top 192a) to a support structure 190.
Figure 12:
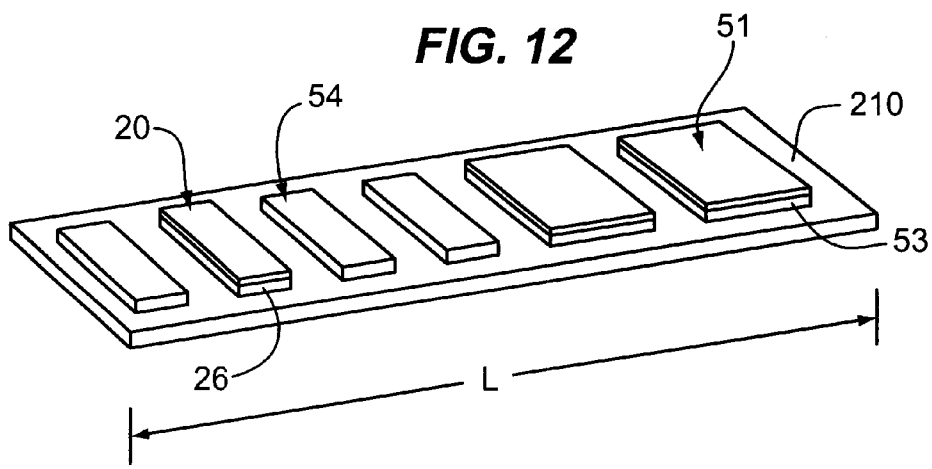
FIG. 12 is an isometric view of an alternate sensing apparatus having several sensor structures ordered in an array fabricated along (here, atop) a support member 210.

FIG. 11B illustrates a alternately-shaped support member 190 having one chamber 192b (with an open entrance 192a) slidably retaining sensor structures 158, 20, and 200. In the slot where structure 158 is positioned, a MHM element could be retained for use to generate an appropriate DC bias field or operate as an ON-OFF switch. FIG. 12 illustrates a simple array structure containing several sensor structures (20, 54, 51) atop a support member 210. Support members 150, 170, 190, 210 are preferably made of machined or otherwise fabricated out of a suitable durable material (such as teflon or plastic) to maintain the ordered array of sensor structures and MHM elements. Use of a magnetostrictive material, here for the support members, may cause unwanted interference with receipt of signals. Overall sizing of such arrays follows principles explained above in connection with desired frequency response and sensing application.

Figure 13A:
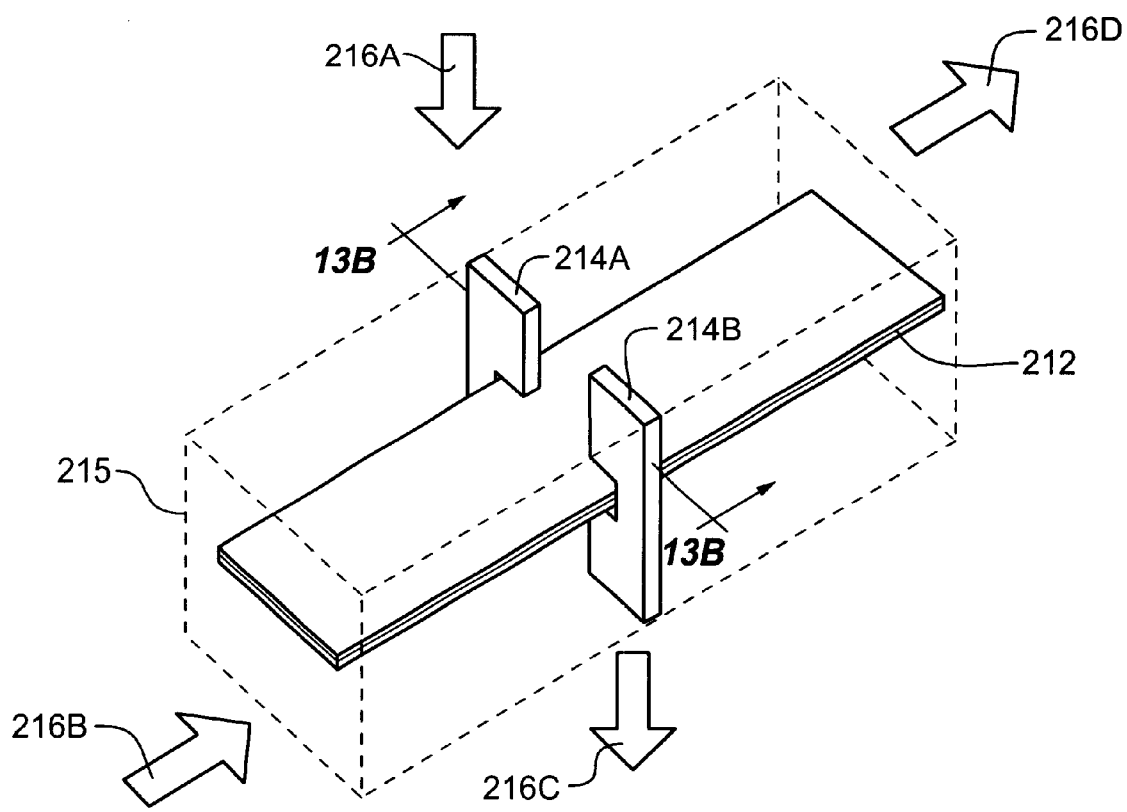
FIG. 13A is an isometric view of an alternate sensor structure 212 retained by a fixture (214a–b) such as can alternatively be used in the viscosity sensing apparatus of the invention.
Figure 13B:
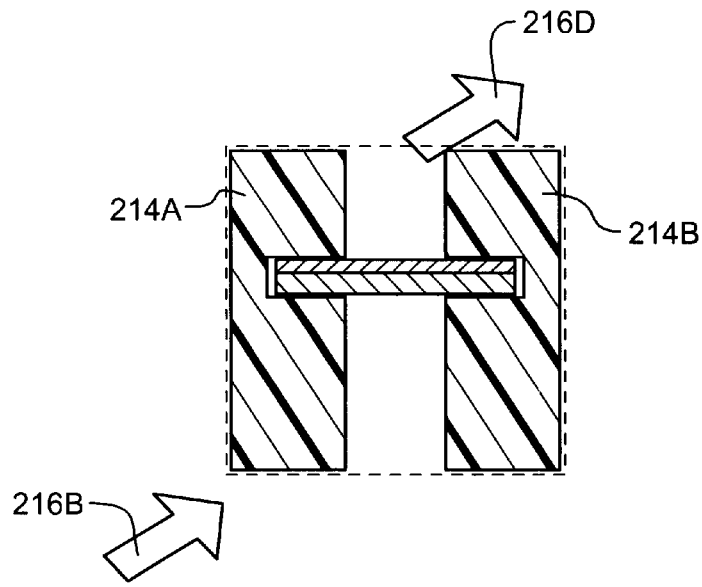
FIG. 13B is a sectional view taken along 13B—13B of FIG. 13A.
Figure 14:
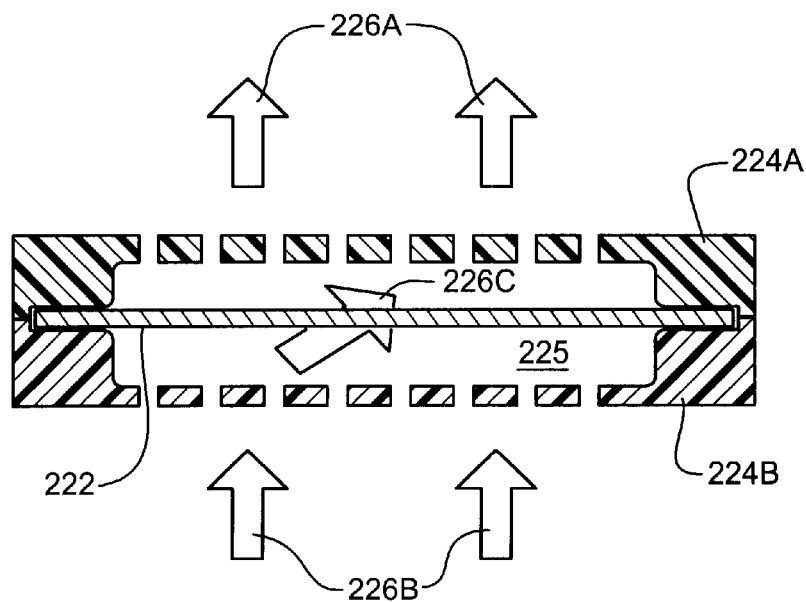
FIG. 14 is a sectional view taken lengthwise of an alternative viscosity sensor fixture design (224a–b) allowing fluid to flow (arrows labeled 226a–b) around sensor structure 222.

FIGS. 13A–B illustrate another sensor structure 212, here retained by fixture components 214a–b positioned, for example, in a housing (shown in phantom at 215) which is preferably perforated, grated, or otherwise open to allow flow of fluid (arrows 216a–d) around the sensor 212. FIG. 14 merely illustrates an alternative way to slidably retain a sensor structure 222 within a chamber 225 of a fixture (in the shape of a clam-shell 224a–b likewise perforated to allow fluid to flow 226a–b around sensor 222). The sensor structures 212, 222 (shown retained by a fixture) work well in the viscosity sensing apparatus of the invention to keep the sensing element from settling flat against a bottom surface or side wall of the environment. Sensor structures 212, 222 could also be shaped (for example, in a arc) to function in the same way. Fixtures 214a–b, 224a–b are preferably made of a suitable plastic or resin and do not tightly clamp the sensor structures. A MHM element (not shown) which can be activated to turn a nearby sensor OFF, or activated to create a DC biased designer-field therearound.

By way of additional example only, and not intended to limit the disclosure hereof, a sensor was designed and built for efficient acoustic response to operate at a resonant frequency, $f_0$, of 40 kHz (to match a commercially available ultrasonic receiver used to receive emissions from the sensor structure). This sensor was cut from a 20 micron layer of METGLAS® 2826 MB magnetostrictive material (commercially distributed) to 3.8 cm×1.8 cm. A mass-changing layer was adhered (brushed on) in a thin film to the METGLAS® base. With $\Delta f$ at 2 kHz (5% $f_0$), the acoustic listening frequencies for the receiver were 38 kHz ($f_0$–$\Delta f$) and 42 kHz ($f_0$+$\Delta f$). The graphical representation at 130 (FIG. 8) best illustrates results from an experimentally-determined pre-correlation of a series of emission intensity ratio values (along the y-axis) taken for this example sensor with corresponding mass change values (along the x-axis) for the sensor to create a relationship for use to identify mass change when this sensor is used in operation in an environment. This pre-correlation, here linear, was found to be independent of orientation within the time-varying interrogating field.

While certain representative embodiments and details have been shown merely for the purpose of illustrating the invention, those skilled in the art will readily appreciate that various modifications may be made to the invention without departing from the novel teachings or scope of this invention. Accordingly, all such modifications are intended to be included within the scope of this invention as defined in the following claims. In the claims, any means-plus-function clauses used are intended to cover the structures described herein as performing the recited function and not only structural equivalents but also equivalent structures.

What is claimed is:

1. An analyte sensing apparatus for operative arrangement within a time-varying magnetic field, comprising:
   a sensor having an outer surface of a material that is chemically responsive to the analyte, said material being adhered to a base magnetostrictive element, said sensor having a magneto-elastic resonant frequency;
   a receiver to measure a first and second value for magneto-elastic emission intensity of said sensor taken at, respectively, a first and second interrogation frequency; and
   a unit to identify a change in mass of said sensor using a ratio of said first and second values.

2. The apparatus of claim 1 wherein said chemically responsive material is adhered over a portion of said base magnetostrictive element by an adhesive layer compatible with both said material and said base magnetostrictive element; and said sensor is incorporated within an array of magnetostrictive elements comprising a viscosity sensing element.

3. The apparatus of claim 1 wherein said first interrogation frequency is less than said magneto-elastic resonant frequency by an interval, $\Delta f$, and said second interrogation frequency is greater than said magneto-elastic resonant frequency by approximately said interval, $\Delta f$.

4. The apparatus of claim 3 wherein said interval, $\Delta f$, is a value between 0.001% and 40% of said magneto-elastic resonant frequency, said magneto-elastic emission is an acoustic emission, said magneto-elastic resonant frequency is an acoustic resonant frequency, and said receiver is an electroacoustic device containing a transducer.

5. The apparatus of claim 1 wherein: said chemically responsive material is a chemically receptive polymer layer having a plurality of microspheres, said chemical responsiveness comprising absorption of subatomic particulate matter from the analyte; and said sensor and a magnetizable magnetically hard element are contained for operation within a chamber of a support member.

6. The apparatus of claim 1 wherein said chemically responsive material is a chemically receptive porous polymer layer, said chemical responsiveness comprising interaction with the analyte causing a change in material stiffness of said sensor, and said base magnetostrictive element extends from a support member from which a second magnetostrictive element also extends to sense viscosity of a fluid therearound.

7. An analyte sensing apparatus for operative arrangement within a time-varying magnetic field, comprising:
   a sensor having an outer surface of a material that is chemically responsive to the analyte, said material being adhered to a base magnetostrictive element, said sensor having a magneto-elastic resonant frequency;
   a receiver to measure a first and second value for magneto-elastic emission intensity of said sensor taken at, respectively, a first and second interrogation frequency, and
   a unit to identify a change in material stiffness of said sensor using a ratio of said first and second values;
   wherein said magneto-elastic resonance frequency is a harmonic of a fundamental resonant frequency of the sensor; and a pre-correlation made between a series of emission intensity ratio values taken for said sensor and a corresponding series of material stiffness values is used for said identification of said change in material stiffness.

8. The apparatus of claim 1 wherein: said chemically responsive material is a sorbent polymer film selected from the group consisting of a poly(isobutylene), ethylene-propylene rubber, poly(isoprene), and poly(butadiene) film; said polymer film is adhered over a substantial portion of said base magnetostrictive element by an adhesive layer compatible with both said polymer film and said base magnetostrictive element; and the analyte is in vapor form.

9. The apparatus of claim 1 wherein said chemically responsive material is an outer polymer hydrogel monolayer reactive to electrostatic forces of subatomic particles within the analyte, and said magnetostrictive element is made of an alloy that remains generally unchanged over a preselected range of temperatures.

10. The apparatus of claim 1 wherein said chemically responsive material is a chemically receptive polymer layer, said chemical responsiveness comprises a loss of matter from said polymer layer, and said base magnetostrictive element is made of an alloy of an element selected from the group consisting of iron, cobalt, samarium, yttrium, gadolinium, terbium, and dysprosium; and further comprising a magnetizable on-off switch comprising a magnetically hard element.

11. The apparatus of claim 1 wherein the analyte is a gas comprising subatomic particles, said chemically responsive material is a zeolite layer, said chemical responsiveness comprises interaction with at least a portion of said subatomic particles to cause a gain in matter of said zeolite layer, said magneto-elastic emission is an acoustic emission, and said receiver is an electroacoustic device containing a transducer.

12. The apparatus of claim 1 wherein:
said first interrogation frequency is less than said magneto-elastic resonant frequency by an interval, $\Delta f$, said second interrogation frequency is greater than said magneto-elastic resonant frequency by approximately said interval, $\Delta f$, said interval being a value between 0.001% and 40% of said magneto-elastic resonant frequency; and
said receiver is an electromagnetic pick-up coil, said magneto-elastic emission is an electromagnetic emission, and said magneto-elastic resonant frequency is a harmonic of a fundamental resonant frequency of said sensor.

13. The apparatus of claim 12 wherein: said chemically responsive material is a chemically receptive polymer layer having a plurality of microspheres which is adhered over a substantial portion of said base magnetostrictive element; said chemical responsiveness comprises swelling of said microspheres as a function of the analyte moisture content; and said sensor is incorporated within an array of magnetostrictive elements comprising a viscosity sensing element.

14. The apparatus of claim 1 further comprising a second sensor having a second resonant frequency different from said magneto-elastic resonant frequency, said second sensor for sensing a viscosity of a fluid therearound; and wherein said receiver is used to measure a third and fourth value for magneto-elastic emission intensity of said second sensor taken at, respectively, a third and fourth interrogation frequency.

15. An analyte sensing apparatus for operative arrangement within a time-varying magnetic field, comprising:
a sensor having an outer surface of a material that is chemically responsive to the analyte, said material being adhered to a base magnetostrictive element;
a receiver to measure a plurality of successive values for magneto-elastic emission intensity of said sensor taken over an operating range of successive interrogation frequencies to identify a magneto-elastic resonant frequency value for said sensor; and
a unit to identify a change in mass of said sensor using said identified magneto-elastic resonant frequency value.

16. The apparatus of claim 15 wherein: said magneto-elastic resonant frequency value corresponds with a relative maximum of said plurality of successive values for magneto-elastic emission intensity measured; and a pre-correlation made between a series of magneto-elastic resonant frequency values for said sensor and a corresponding series of mass change values for said sensor is used for said identification of said change in mass.

17. The apparatus of claim 15 wherein: said magneto-elastic emission is an acoustic emission, and said receiver is an electroacoustic device containing a transducer for operation over a range of frequencies from 1 KHz to 1 GHz; said chemically responsive material is a chemically receptive polymer layer, said chemical responsiveness comprising absorption of subatomic particulate matter from the analyte causing an increase in said mass and a change in material stiffness of said sensor; and further comprising a magnetizable on-off switch comprising a magnetically hard element.

18. The apparatus of claim 15 wherein:
said magneto-elastic emission is an acoustic emission, and said receiver is an electroacoustic device containing a transducer;
said chemically responsive material is a polymer layer having swellable gel membrane complexes, said chemical responsiveness comprising diffusion of selected ion species of the analyte into said polymer layer to sense glucose concentration; and
a pre-correlation made between a series of acoustic resonant frequency values for said sensor and a corresponding series of mass change values for said sensor is used for said identification of said change in mass.

19. The apparatus of claim 15 wherein said receiver is an electromagnetic pick-up coil, said magneto-elastic emission is an electromagnetic emission, said magnetostrictive element is elongated in shape, and further comprising, in proximity to said sensor, a magnetizable magnetically hard element for generating a DC bias field.

20. The apparatus of claim 15 further comprising a second sensor for sensing temperature, both said sensors extending from a support member; said receiver to further measure a second plurality of successive values for magneto-elastic emission intensity of said second sensor taken over a second operating range of successive interrogation frequencies to identify a magneto-elastic resonant frequency value for said second sensor.

21. A method of sensing an analyte with a sensor having a chemically responsive material adhered to a base magnetostrictive element, the sensor having a magneto-elastic resonant frequency, comprising the steps of:
applying a time-varying magnetic field;
measuring a first and second value for magneto-elastic emission intensity of the sensor with a receiver operating at, respectively, a first and second interrogation frequency; and
using a ratio of said first and second values to identify a change in mass, of the sensor due to the chemical responsiveness of said sensor to said analyte.

22. The method of claim 21 wherein said first interrogation frequency is less than the magneto-elastic resonant frequency by an interval, $\Delta f$, and said second interrogation frequency is greater than the magneto-elastic resonant frequency by approximately said interval; said interval being a value between 0.001% and 40% of the magneto-elastic resonant frequency.

23. The method of claim 21 wherein said chemically responsive material is a polymer layer, the chemical responsiveness comprising absorption of subatomic particulate matter from the analyte, said receiver is an electroacoustic device containing a transducer to aid in said step of measuring; and further comprising, prior to said step of using, the step of pre-correlating a series of emission intensity ratio values taken for the sensor and a corresponding series of mass values for the sensor.

24. The method of claim 23 wherein said polymer layer is a hydrogel reactive to electrostatic forces of said subatomic particulate matter, said step of pre-correlating is used for said step to identify a change in mass, and further comprising the step of applying a known relationship between said change in mass and the analyte for the sensing thereof.

25. The method of claim 21 wherein said receiver is an electromagnetic pick-up coil, said magneto-elastic emission is an electromagnetic emission, said chemically responsive material is a layer which is adhered over a portion of said base magnetostrictive element by an adhesive compatible with both said layer and said element, and said element is made of an alloy that remains generally unchanged over a preselected range of temperatures; and further comprising, using said ratio of first and second values to identify a change in material stiffness, if any, of the sensor due to the chemical responsiveness.

26. The method of claim 21 further comprising the step of measuring a third and fourth value for magneto-elastic emission intensity of a second sensor with said receiver operating at, respectively, a third and fourth interrogation frequency to sense a viscosity of a fluid therearound; both said sensors extending from a support member in an ordered array.

27. A method of sensing an analyte with a sensor having a chemically responsive material adhered to a base magnetostrictive element, comprising the steps of:
  applying a time-varying magnetic field;
  measuring a plurality of successive values for magneto-elastic emission intensity of the sensor with a receiver operating over a range of successive interrogation frequencies to identify a magneto-elastic resonant frequency value for the sensor;
  pre-correlating a series of resonant frequency values taken for the sensor and a corresponding series of mass values for the sensor; and
  using said identified magneto-elastic resonant frequency value and said step of pre-correlating to identify a change in mass, of the sensor.

28. The method of claim 27 wherein: said receiver is an electroacoustic device containing a transducer to aid in said step of measuring, said magneto-elastic emission is an acoustic emission, said magneto-elastic resonant frequency value corresponds with a relative maximum of said plurality of successive values for magneto-elastic emission intensity measured; and further comprising the step of applying a known relationship between said change in mass and the analyte for the sensing thereof.

29. A method of sensing an analyte with a sensor having a chemically responsive material adhered to a base magnetostrictive element comprising the steps of:
  applying a time-varying magnetic field;
  applying a DC bias magnetic field;
  measuring a plurality of successive values for magneto-elastic emission intensity of the sensor with a receiver operating over a range of successive interrogation frequencies to identify a magneto-elastic resonant frequency value for the sensor;
  pre-correlating a series of resonant frequency values taken for the sensor and a corresponding series of material stiffness values for the sensor; and
  using said identified magneto-elastic resonant frequency value and said step of pre-correlating to identify a change in material stiffness of the sensor;
  wherein said receiver is an electromagnetic pick-up coil and said element is made of an alloy that remains generally unchanged over a preselected range of temperatures.

30. The method of claim 27 further comprising the steps of measuring a second plurality of successive values for magneto-elastic emission intensity of a second sensor with said receiver operating over a second range of successive interrogation frequencies to identify a magneto-elastic resonant frequency value for said second sensor, and pre-correlating a second series of resonant frequency values taken for said second sensor and a corresponding second series of viscosity values for a fluid surrounding said second sensor.

* * * * *